(12) United States Patent
Holmqvist

(10) Patent No.: US 10,357,612 B2
(45) Date of Patent: Jul. 23, 2019

(54) PLUNGER SEGMENTS DRIVE MECHANISM FOR A MEDICAMENT DELIVERY DEVICE

(71) Applicant: Carebay Europe LTD, Swatar (MT)

(72) Inventor: Anders Holmqvist, Varmdo (SE)

(73) Assignee: SHL Medical AB, Zug (CH)

( * ) Notice: Subject to any disclaimer, the term of this patent is extended or adjusted under 35 U.S.C. 154(b) by 126 days.

(21) Appl. No.: 15/317,073

(22) PCT Filed: May 11, 2015

(86) PCT No.: PCT/EP2015/060360
§ 371 (c)(1),
(2) Date: Dec. 7, 2016

(87) PCT Pub. No.: WO2015/188997
PCT Pub. Date: Dec. 17, 2015

(65) Prior Publication Data
US 2017/0119972 A1 May 4, 2017

(30) Foreign Application Priority Data
Jun. 10, 2014 (SE) ...................... 1450704

(51) Int. Cl.
*A61M 5/315* (2006.01)
*A61M 5/20* (2006.01)
*A61M 5/32* (2006.01)
*A61M 5/48* (2006.01)

(52) U.S. Cl.
CPC ...... *A61M 5/31511* (2013.01); *A61M 5/2033* (2013.01); *A61M 5/315* (2013.01); *A61M 5/3158* (2013.01); *A61M 5/3202* (2013.01); *A61M 5/484* (2013.01); *A61M 5/31591* (2013.01); *A61M 2005/2013* (2013.01); *A61M 2005/2073* (2013.01); *A61M 2005/2086* (2013.01)

(58) Field of Classification Search
CPC ............ A61M 5/2033; A61M 5/31511; A61M 5/3158; A61M 2005/2086; A61M 5/315; A61M 5/484
See application file for complete search history.

(56) References Cited

U.S. PATENT DOCUMENTS
2007/0185437 A1  8/2007  Goldenberg et al.

FOREIGN PATENT DOCUMENTS
DE   8326217.2 U1   12/1983
DE   10160393 A1   6/2003
WO   2006066963 A1   6/2006
(Continued)

*Primary Examiner* — Rebecca E Eisenberg
(74) *Attorney, Agent, or Firm* — McDonnell Boehnen Hulbert & Berghoff LLP

(57) ABSTRACT

The present invention relates to a drive mechanism (10; 177) for a medicament delivery device, which drive mechanism (10; 177) comprises an elongated plunger rod (12; 176), wherein the plunger rod comprises a number of discrete segments (14; 178), interlocking elements (18, 20, 32, 34, 60, 62; 182, 184, 196, 198, 212, 214) arranged between adjacent segments operably arranged to releasably locking adjacent segments, drive force elements (30, 50 71; 194, 210, 230) operably arranged to act between adjacent segments, and release elements (46, 68; 208, 228) operably arranged to act on said interlocking elements (18, 20, 32, 34, 60, 62; 182, 184, 196, 198, 212, 214) such that said segments (14; 178) are released in sequence.

14 Claims, 21 Drawing Sheets

(56) References Cited

FOREIGN PATENT DOCUMENTS

| WO | 2011123024 A1 | 10/2011 |
| WO | 2013028906 A1 | 2/2013 |
| WO | 2013119591 A1 | 8/2013 |

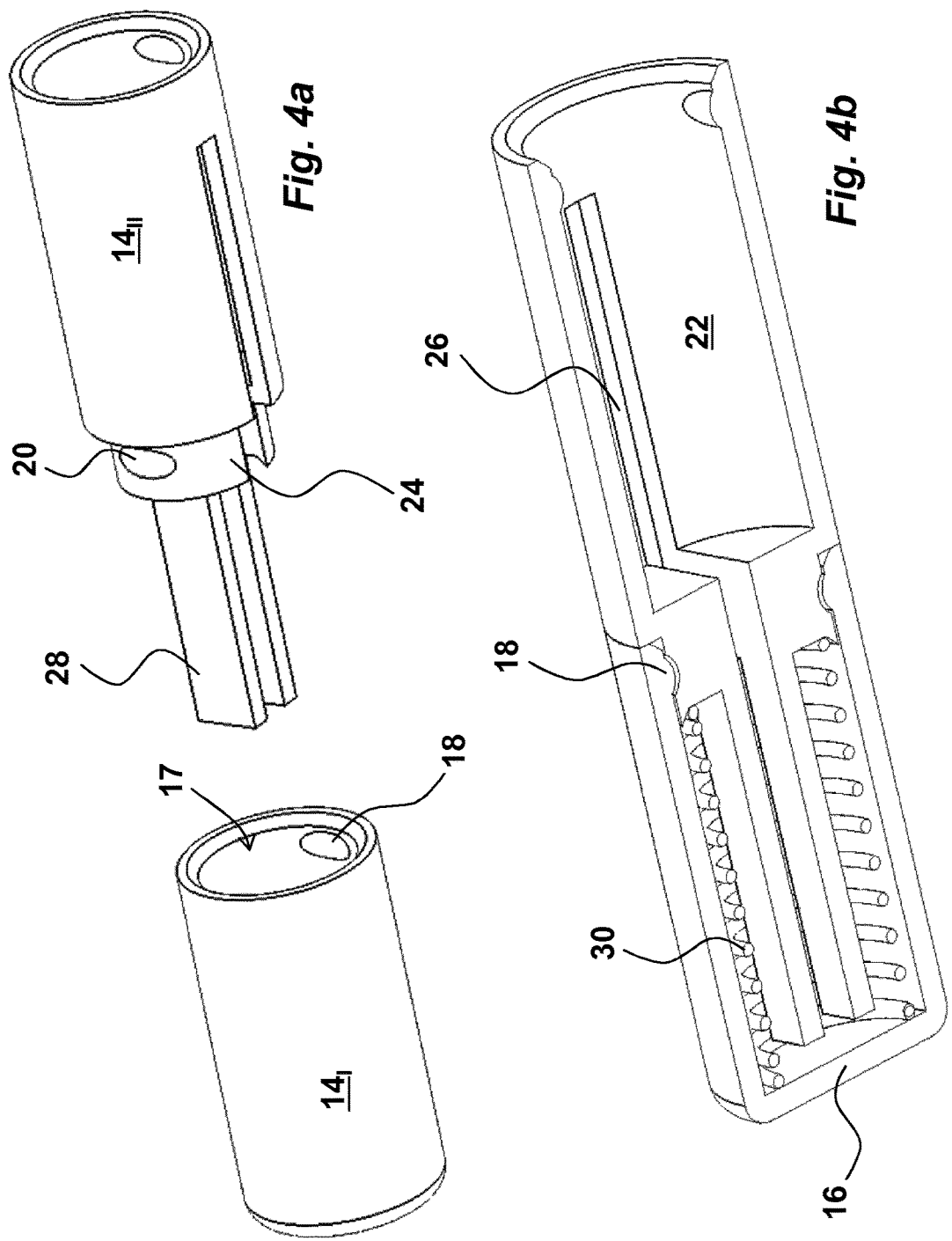

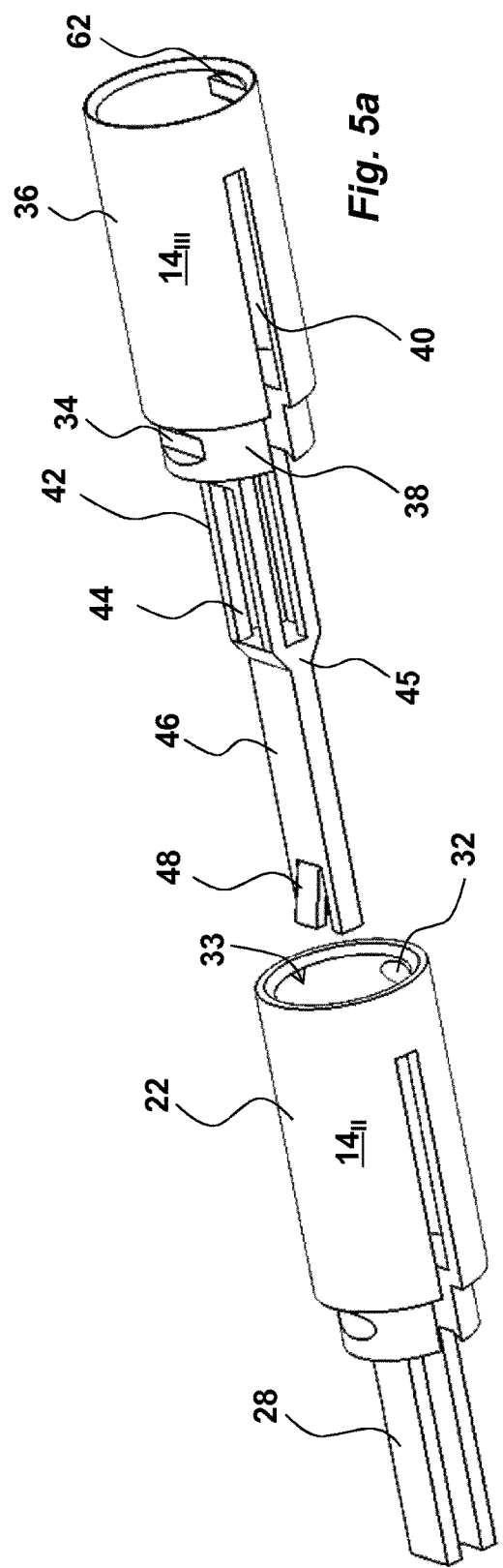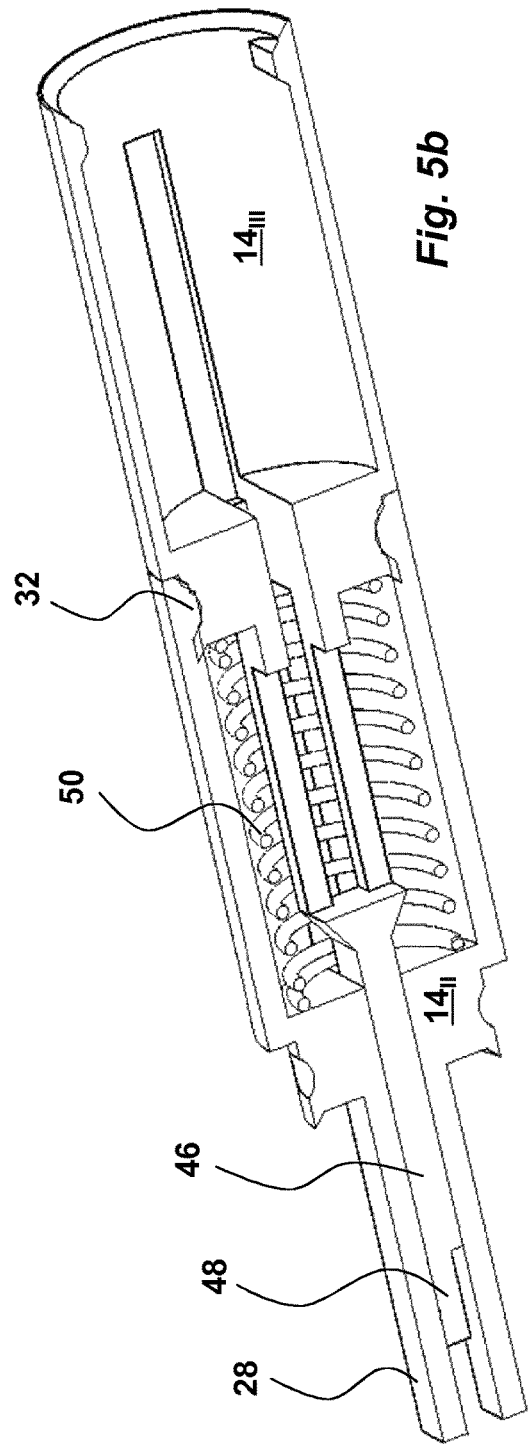

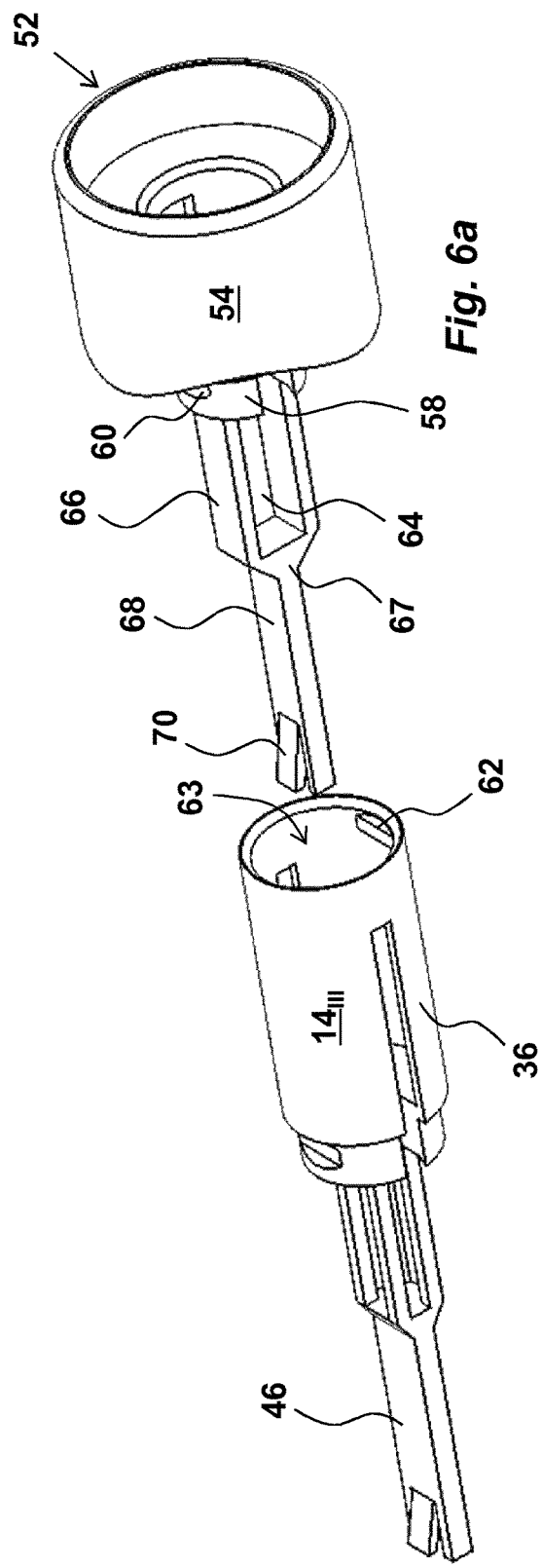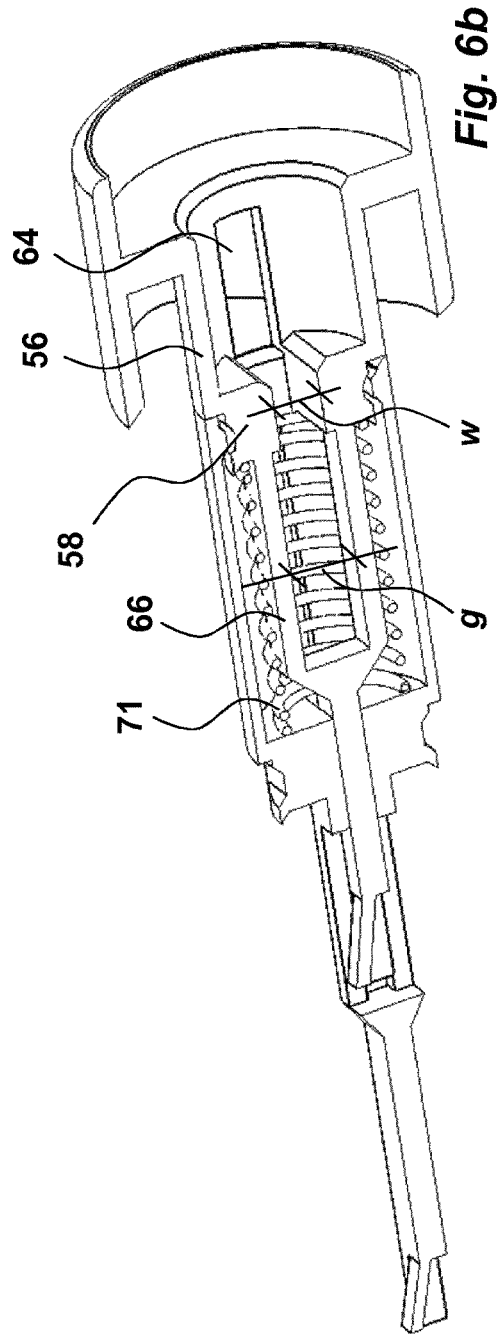

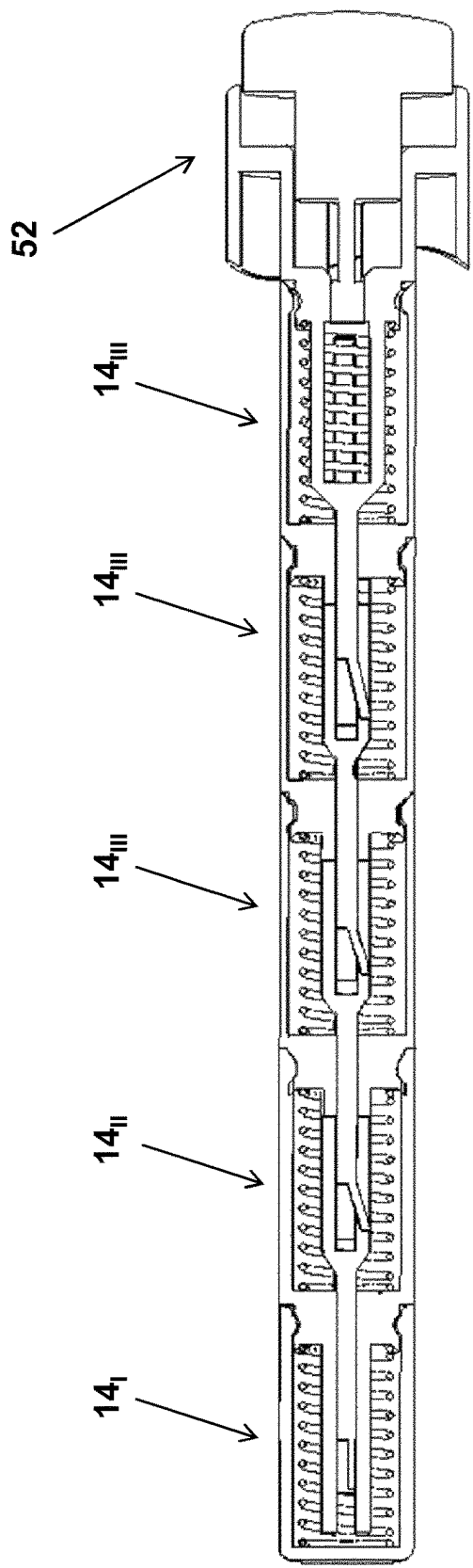
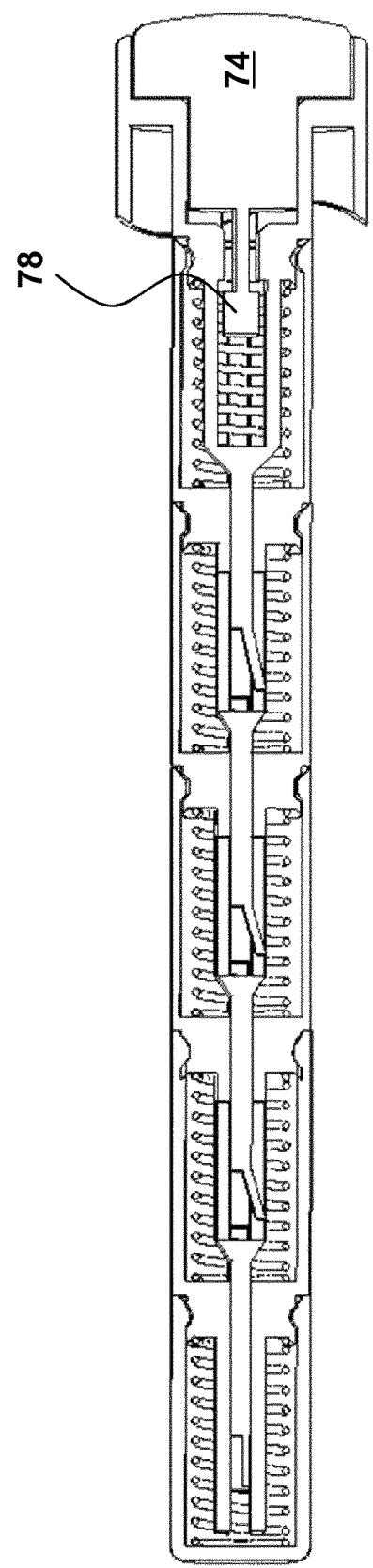
Fig. 8a
Fig. 8b

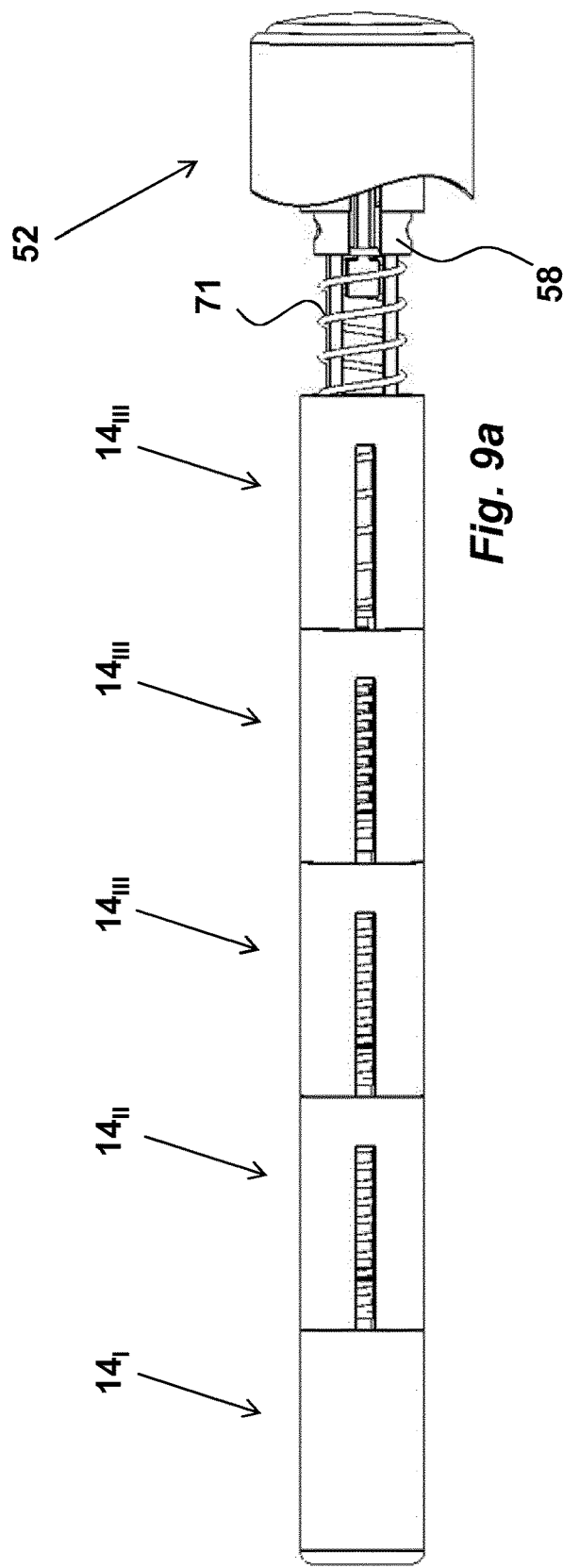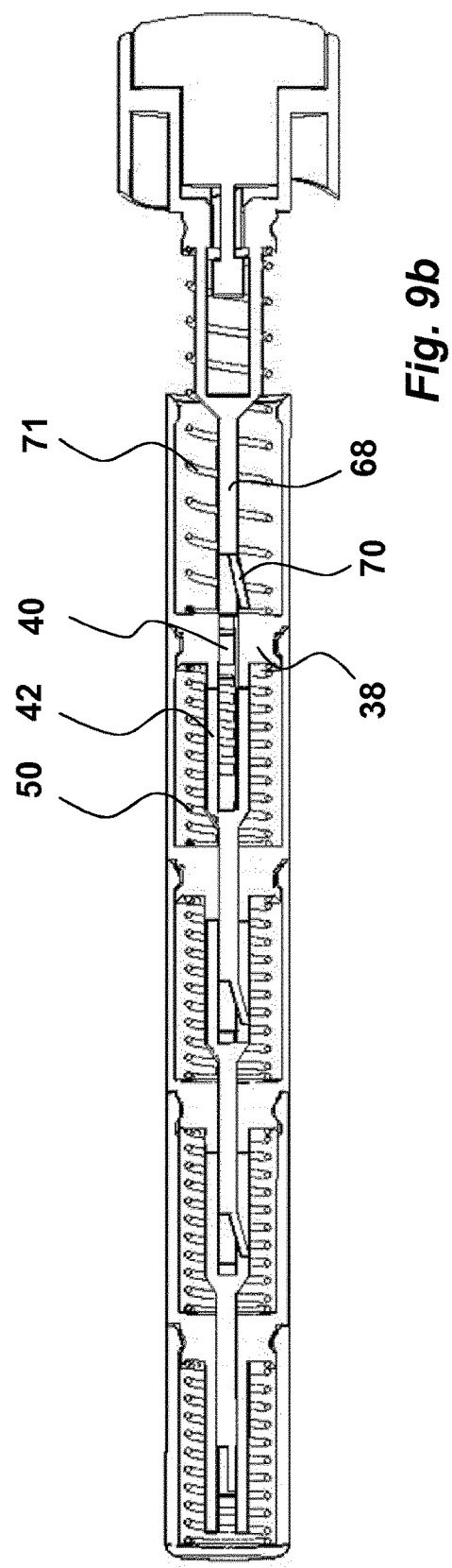

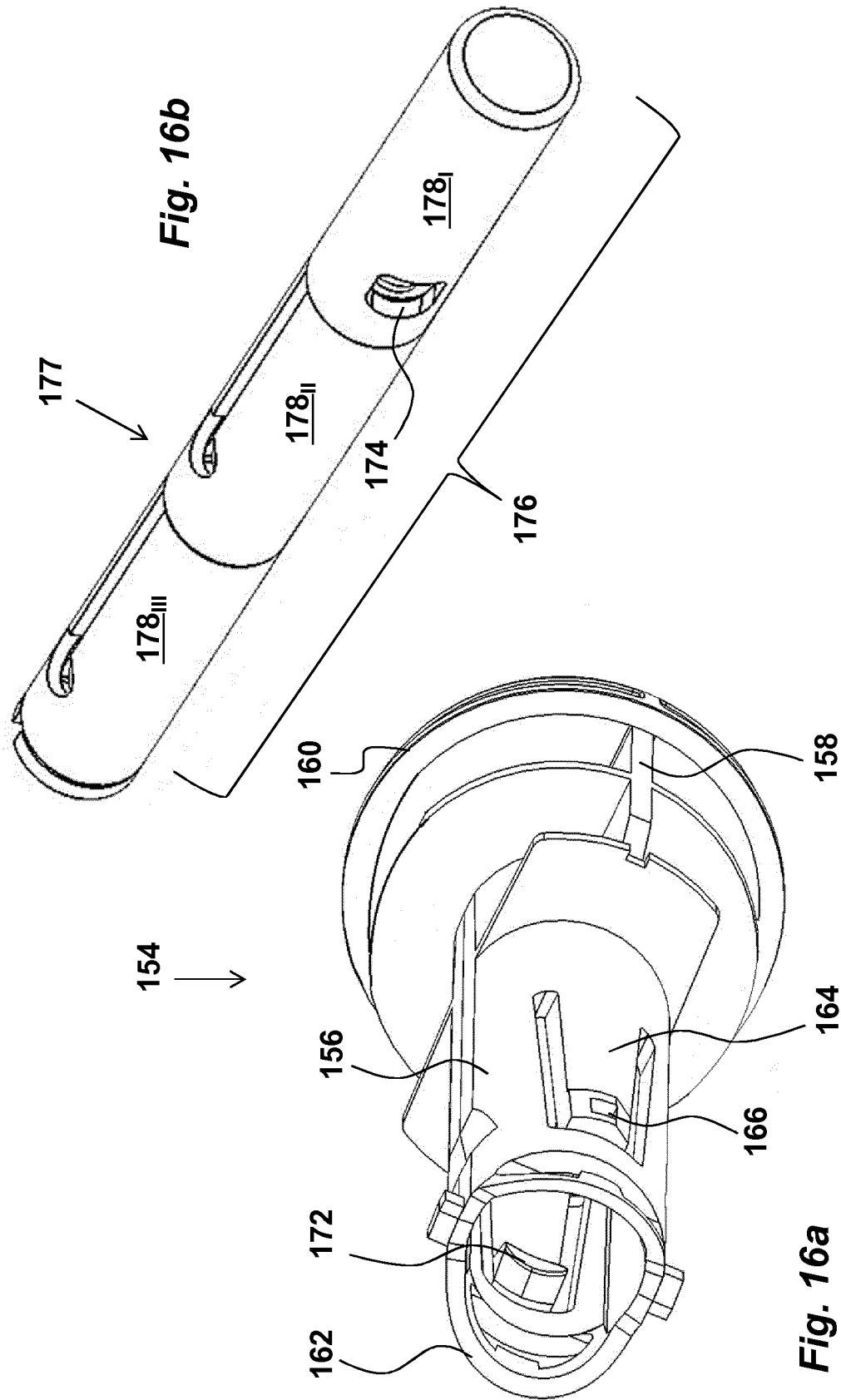

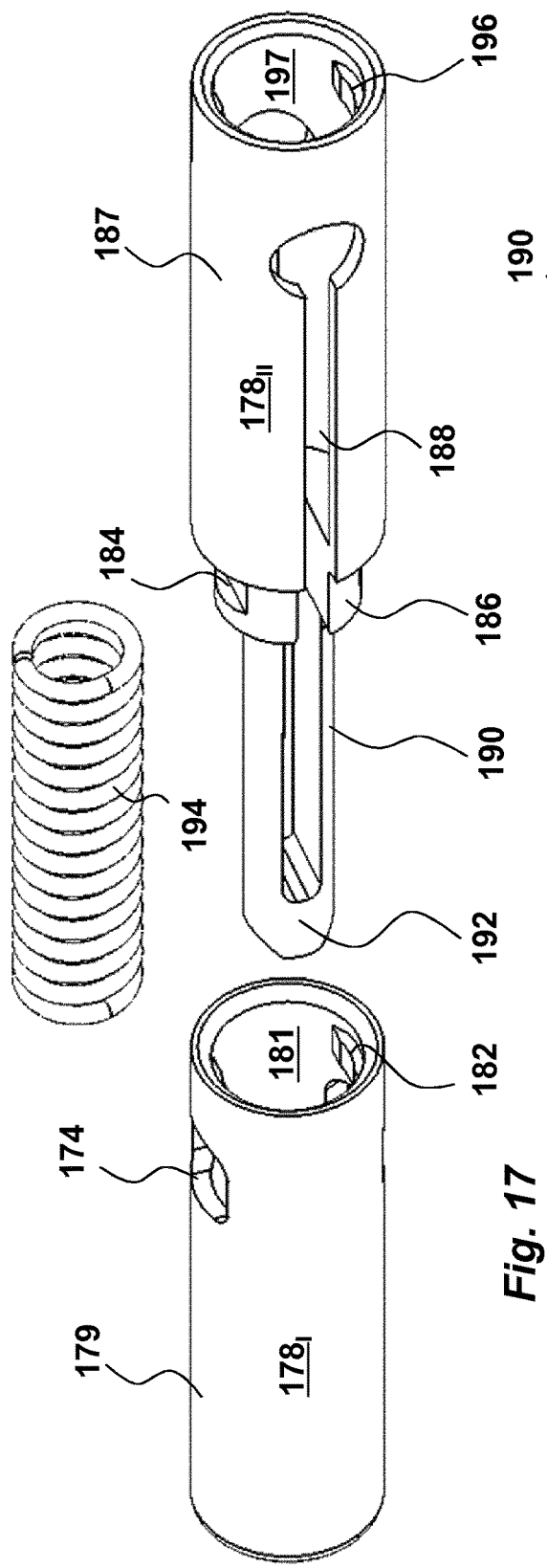
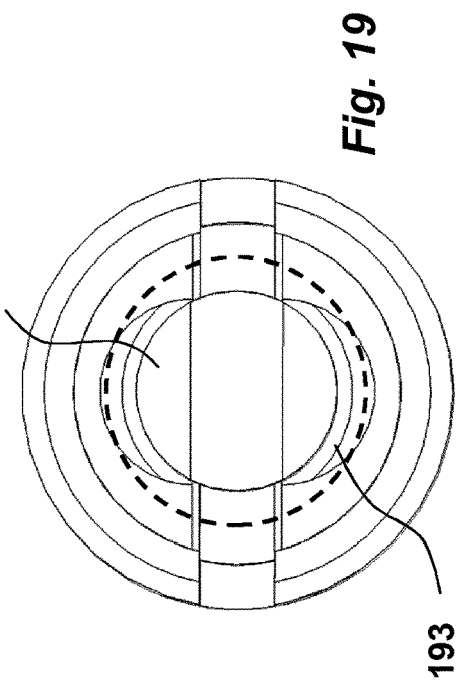
Fig. 19
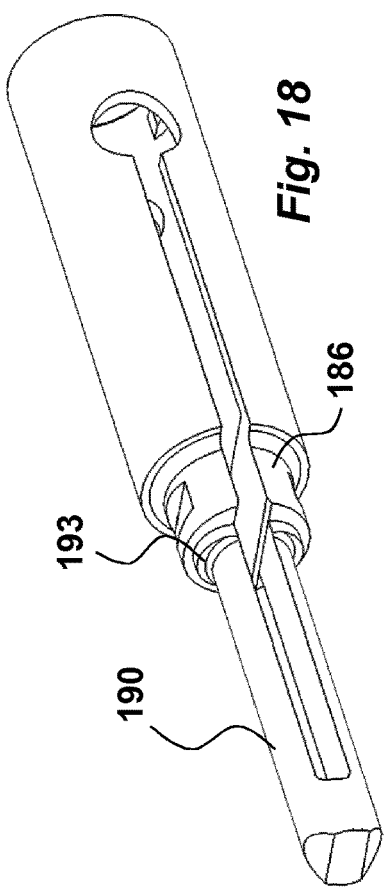
Fig. 18
Fig. 17

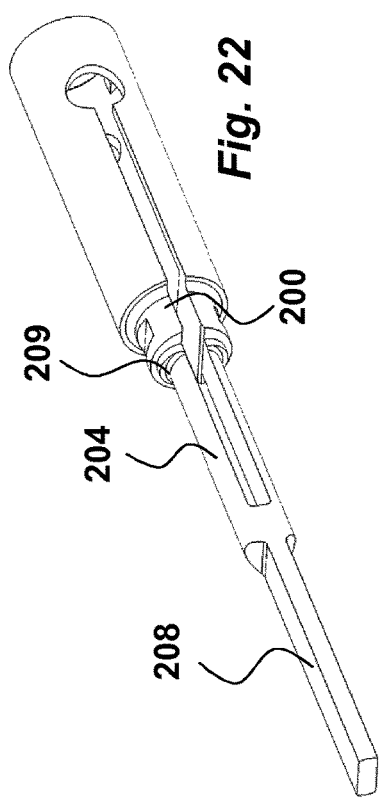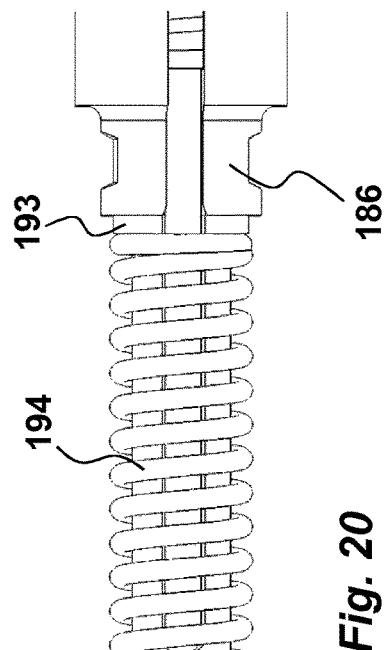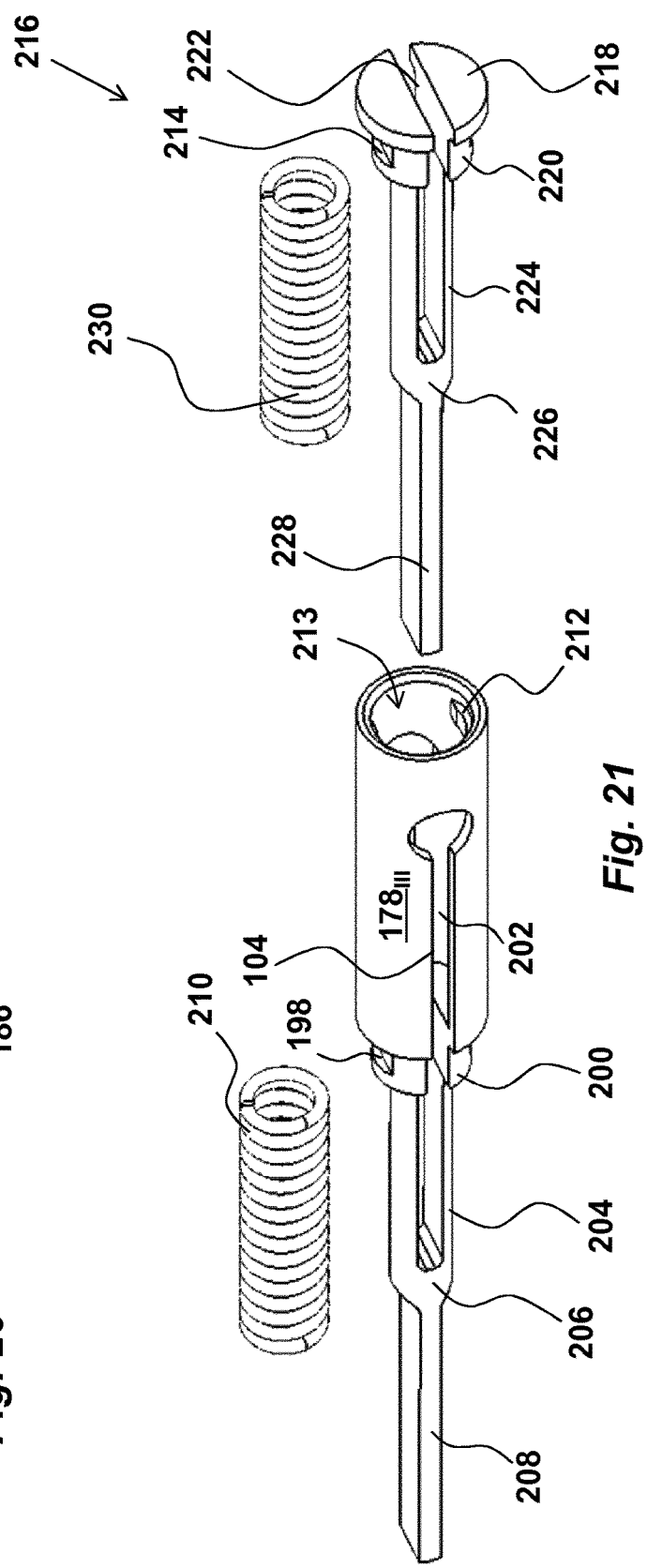

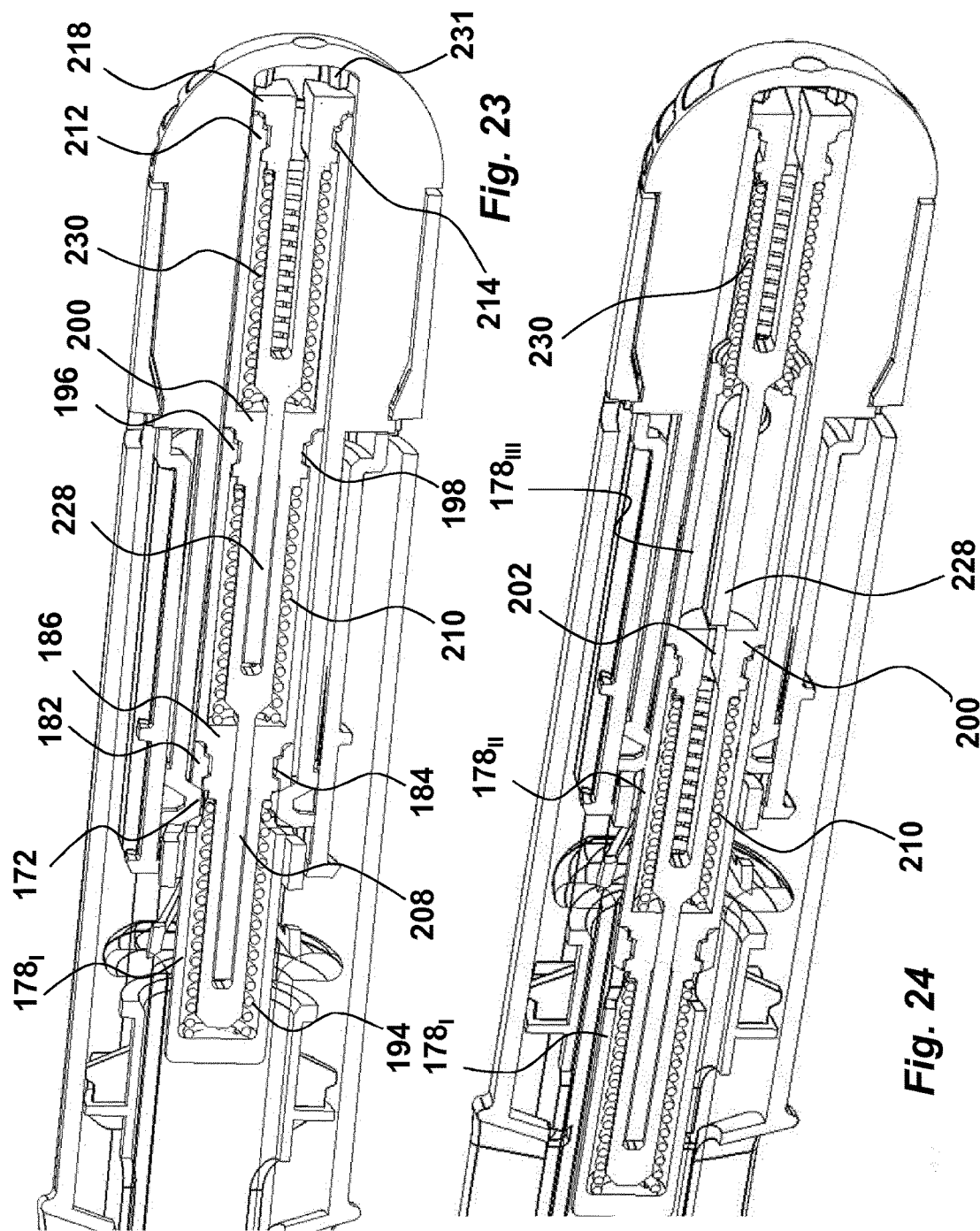

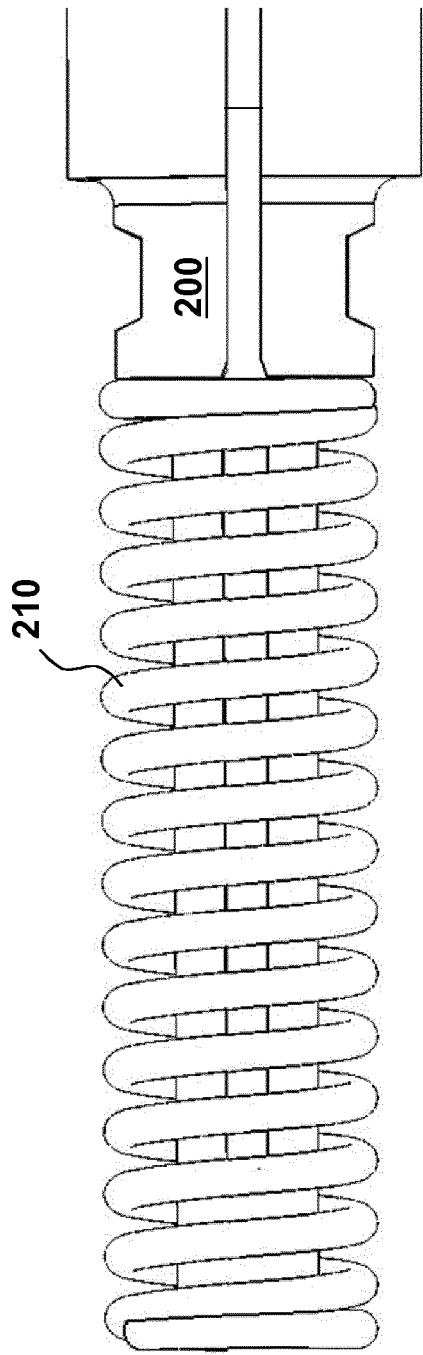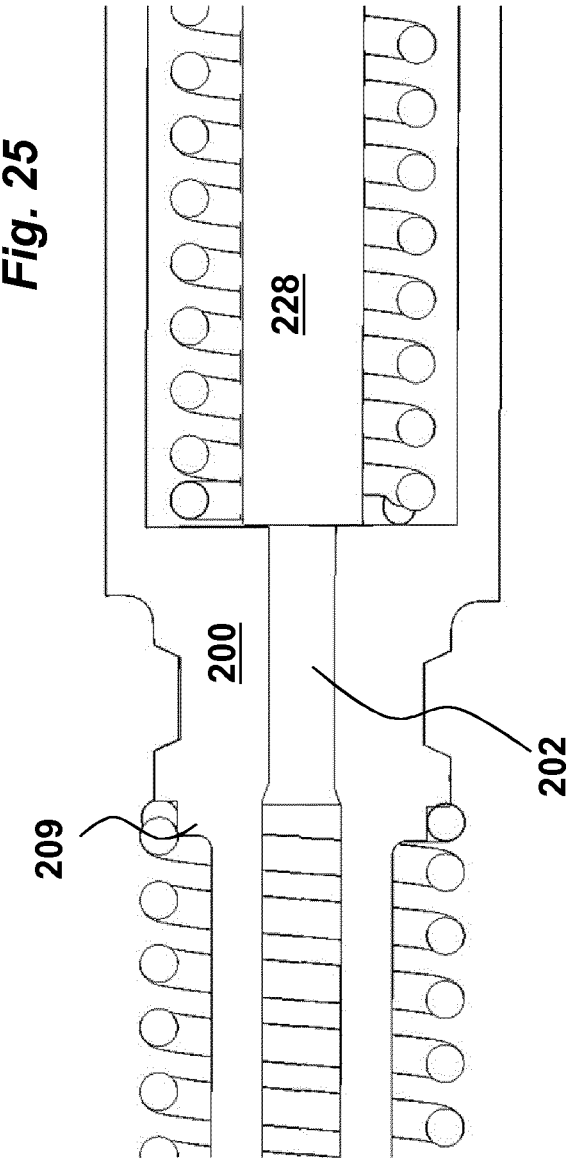
*Fig. 25*
*Fig. 26*

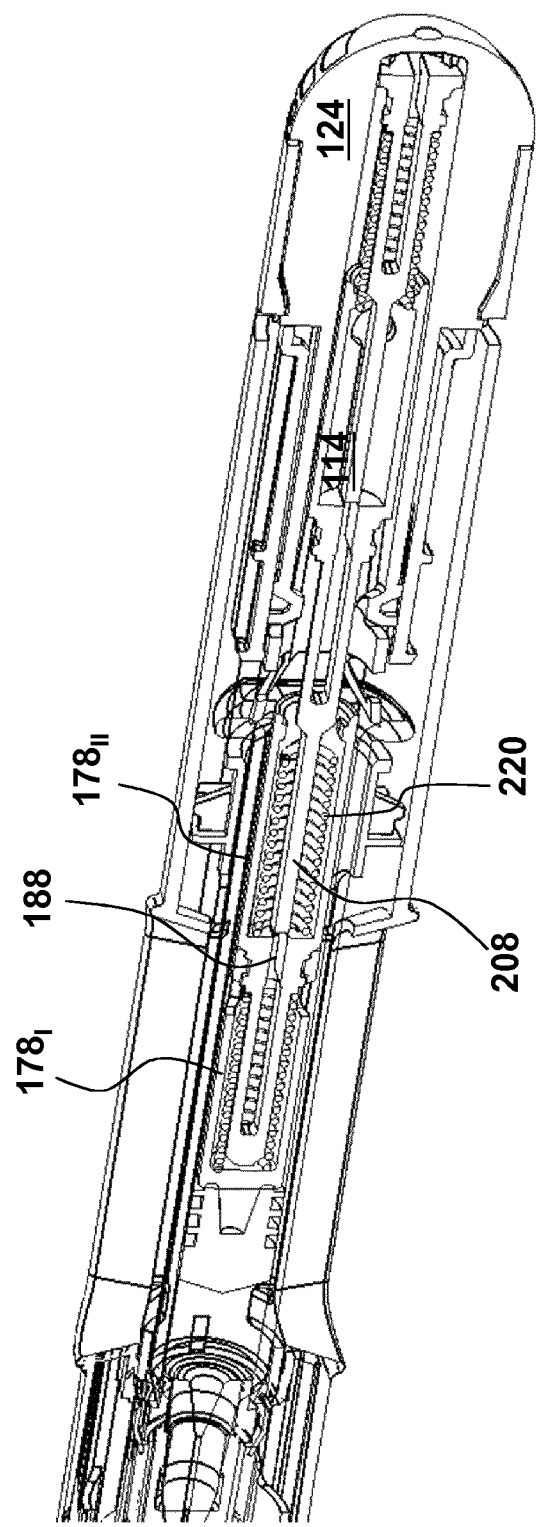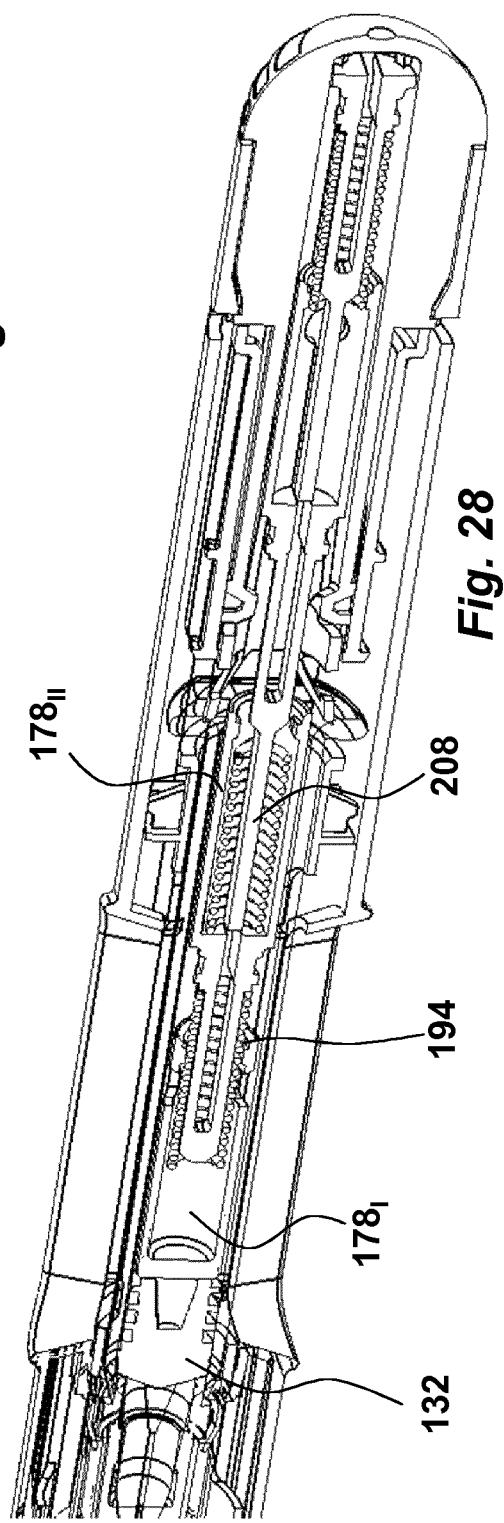

US 10,357,612 B2

PLUNGER SEGMENTS DRIVE MECHANISM FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2015/060360 filed May 11, 2015, which claims priority to Swedish Patent Application No. 1450704-0 filed Jun. 10, 2014. The entire disclosure contents of these applications are herewith incorporated by reference into the present application.

TECHNICAL AREA

The present invention relates to a drive mechanism intended for a medicament delivery device, which drive mechanism is capable of delivering a force to a medicament container throughout a medicament dose delivery sequence.

BACKGROUND OF INVENTION

A vast majority of medicament delivery devices developed and brought to the market are provided with drive mechanisms that are arranged to act on a medicament container for expelling a dose of medicament through a dose delivery member. Many medicament containers are designed as elongated tubes, often made of glass. A proximal end of the container is arranged with a medicament delivery member, such as a needle, or with attachment means for a medicament delivery member. At the distal end of the medicament container, a resilient stopper is arranged which seals the container. Pressure is applied to the contents of the medicament container via a plunger rod comprised in the drive mechanism. The resilient stopper is often made of rubber or a soft plastic.

As stated above, the drive mechanism often comprises an elongated plunger rod arranged to act on the stopper of the medicament container. In turn, a drive spring is often operably connected to the plunger rod. In a majority of cases, the drive spring is a conventional compression spring. Compression springs are capable of delivering a force that is initially high when the spring is compressed. Thereafter the force decreases linearly during the dose delivery sequence as the spring extends.

The decreasing force causes the stopper to slow down and thus the dose delivery time per volume unit increases, which leads to slow dose delivery at the end of the dose delivery sequence. In some cases, the force requirement is greatest at the end of the plunger rod stroke due to poor siliconization etc. In order to cope with such problems, excessively powerful springs are used, which in turn increase the risk of breaking the medicament container at the start of the dose delivery sequence.

Document US 2007/0185437 discloses a needleless injector. According to some embodiments, the injector may have two or three sources of energy. The main source is a conventional compression spring that is arranged to push a plunger rod, thereby acting on a stopper for delivering a dose of medicament. A chamber with compressed gas is further operatively connected to the plunger rod. The idea is that when the plunger rod is released, the compression spring will urge the plunger rod in the proximal direction, impacting the stopper. At a certain position of the plunger rod the gas chamber is activated so that the compressed gas will also act on the stopper. The combined forces will provide a more uniform pressure and velocity during dose delivery.

A major drawback of US 2007/0185437 is the use of compressed gas as an energy source. It requires very precise tolerances and therefore expensive sealing solutions that are not feasible for most medicament delivery devices, especially not for disposable devices, where the cost per unit would be far too high. Another drawback is that the stroke length during which the compressed gas acts is rather short. If a more continuous force distribution is required for a longer stroke, compressed gas is not an option. The use of a chamber of compressed gas positioned at a proximal end of the plunger rod also adds to the overall length of the device, which can be a critical aspect of some devices.

A solution for reducing the overall length of a device is disclosed in WO 2006/066963. The plunger rod is made of a number of segments that are rotatable in relation to each other. The segments are arranged with surfaces abutting adjacent segments, which surfaces are inclined. This causes the segments to move in a proximal direction when they are turned relative each other such that the plunger rod is extended, whereby a dose of medicament may be delivered by the extension of the plunger rod.

A drawback with the solution of WO 2006/066963 is that the operation and the extension of the plunger rod is completely manual, i.e. there is no power source that aids a user when delivering a dose of medicament. Further, inclined surfaces of the segments provide a rather complex technical solution that could be rather costly.

BRIEF DESCRIPTION OF INVENTION

In the present application, when the term "distal part/end" is used, this refers to the part/end of the device, or the parts/ends of the members thereof, which during use of the device is located the furthest away from the medicament delivery site of the patient. Correspondingly, when the term "proximal part/end" is used, this refers to the part/end of the device, or the parts/ends of the members thereof, which during use of the device is located closest to the medicament delivery site of the patient.

The aim of the present invention is to remedy the drawbacks of the state of the art devices. This aim is obtained by a drive mechanism having the features of the independent patent claim. Preferable embodiments of the invention form the subject matter of the dependent patent claims.

According to a major aspect of the invention it may comprise a drive mechanism for a medicament delivery device, which drive mechanism comprises an elongated plunger rod. The plunger rod may comprise a number of discrete segments, from at least two up to a plurality, depending on the requirements of the particular use. The segments may be provided with interlocking elements arranged between adjacent segments operably arranged to releasably lock adjacent segments, in order to make the segments capable of being locked to each other until activation.

Further, the drive mechanism may be arranged with drive force elements operably arranged to act between adjacent segments. In this respect, the drive force elements may have a number of different shapes and forms for providing a force between adjacent segments. One feasible solution of a drive force element is a compression spring, but other types of springs such as gas springs, disc springs, etc, may be used.

Also, the force output from the drive force elements may be varied between segments of the drive mechanism depending on the force requirements. In some applications, or instance, it is desirable to have a rather weak force at the start of a injection sequence and to have stronger force at the end. Drive force elements of different drive forces may be used between the segments.

In order to obtain the desired function of the drive mechanism, it may be arranged with release elements operably arranged to act on the interlocking elements such that said segments are released in sequence. The sequential release provides a more even force distribution during the whole movement of the plunger rod in compared to using a single drive force element. Further, the sequential function allows the use of a plurality of drive force elements having different force characteristics.

According to an aspect of the drive mechanism, the interlocking elements may comprise form-engaging elements, such as protrusions and recesses arranged on adjacent segments and arranged generally radially in relation to each other. The use of form-engaging elements provides for a simple yet sturdy solution where many different structural shapes may be utilised for obtaining the desired function.

In that respect, the interlocking elements may be arranged such that the radially innermost of the interlocking elements is movable inwards in the generally radial direction. The solution provides a lock and release function that is obtained by holding or moving the innermost element in a radial direction. Also, the release elements may be operably connected to the innermost interlocking elements such as to prevent inwards movement until activation of the drive mechanism.

According to another aspect of the drive mechanism, the elements may be operably connected to an adjacent, distally positioned, segment. This provides the possibility of operating in sequence in that the distally positioned segment is the segment that releases the adjacent, proximal, segment. In that respect, according to a solution, a proximally positioned segment may be arranged with a passage in its distal end, and whereby an adjacent, distally positioned, segment is arranged with a protrusion fitting into said passage, which protrusion comprises the release elements.

The protrusion may then be arranged flexible in a generally radial direction and the release element may comprise an elongated element in contact with the protrusion for preventing flexing in the generally radial direction. In that respect, the flexible arrangement may comprise at least one generally longitudinally extending slit, which at least one slit divides the protrusion in at least two parts, and wherein the elongated element extends into said slit. The slit provides the flexing function while the elongated element provides the hold and release function. Thus the slit of a proximal segment is affected by an elongated element of an adjacent distal segment, thereby providing the desired sequential function of the drive mechanism.

According to another aspect of the drive mechanism, it may further comprise support elements arranged to support a segment when a proximally positioned segment is activated. By this solution, the support elements may prevent movement in the distal direction. This can be important in that when a proximally positioned segment is released and its drive force element acts between the released segment and the adjacent distal segment, the force must not urge the distal segment in the distal direction. Instead, the support element prevents distal movement and creates a force support.

According to another aspect of the drive mechanism, the support element may be comprised in the elongated element, making use of the design of the segments. In that respect, the support element may comprise a proximally directed surface. Further, the proximally directed surface may be arranged on a flexing arm, which arm flexes in a generally transversal direction when the elongated element is moved out of contact with the slit. The flexing action then provides a biasing of the support surface from the slit to an adjacent surface of the proximal segment, thereby providing the support and prevention of movement in a distal direction.

According to another aspect of the drive mechanism, the drive force elements may be operably arranged such that the gap of the slit is reduced when the elongated element is moved out of the slit. The elongated element cannot then re-enter the slit and its proximal surface will be in contact with a surface adjacent the slit of the proximal segment, thereby providing the support and prevention of movement in a distal direction.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIGS. 2-7 show detailed views of components comprised in the drive mechanism of FIG. 1, FIGS. 8-10 show different functional positions of the drive mechanism of FIG. 1.

DETAILED DESCRIPTION OF THE INVENTION

Figure 1:
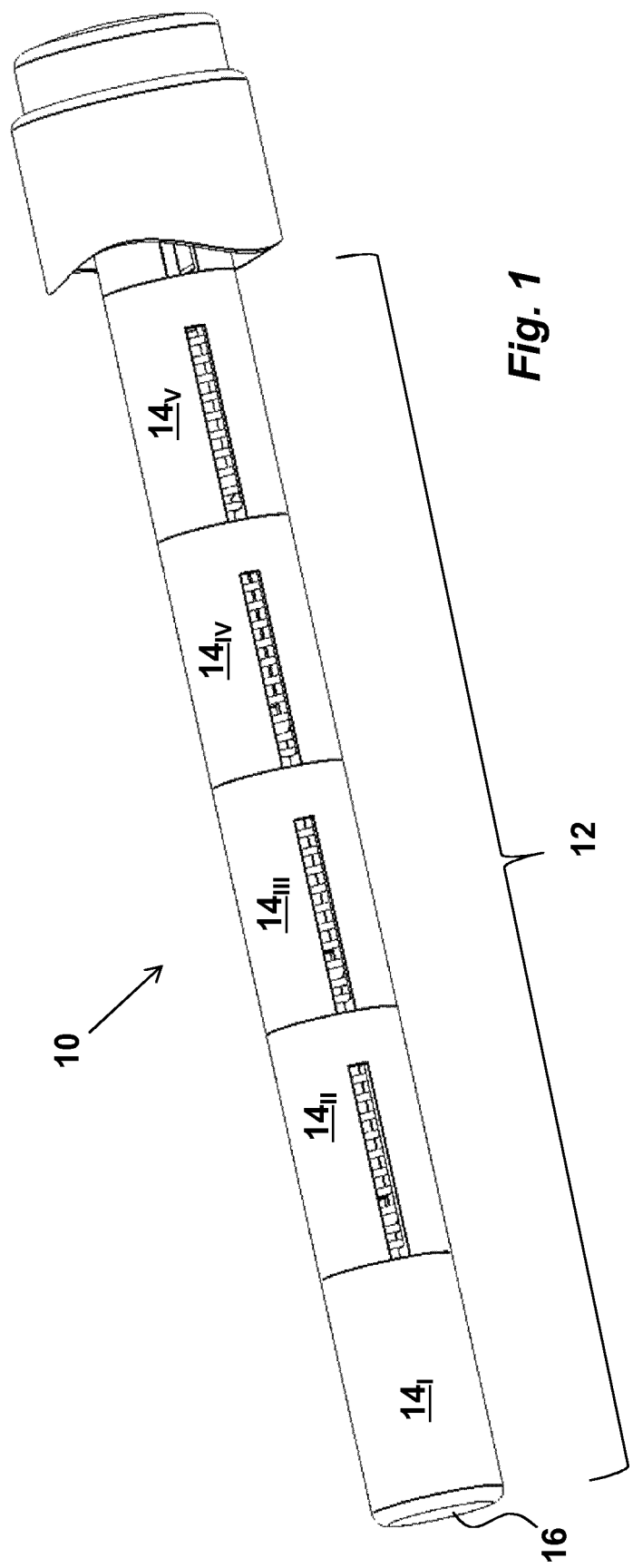
FIG. 1 shows an example of a drive mechanism according to the present invention.

A drive mechanism 10 is disclosed in FIG. 1. It comprises an elongated plunger rod 12. According to the invention the plunger rod 12 is made of a number of discrete segments 14 that are releasably interconnected to each other as will be described. The most proximal segment, hereafter named the first segment $14_I$, is arranged with an end surface 16 intended to be in contact with a stopper in a medicament container. The first segment $14_I$ is generally tubular and is arranged with a distally directed passage 17 having interlocking elements, in the embodiments shown two protrusions 18 on its inner surface, FIGS. 2 and 4, which protrusions 18 are positioned generally diametrically opposite each other.

Figure 2:
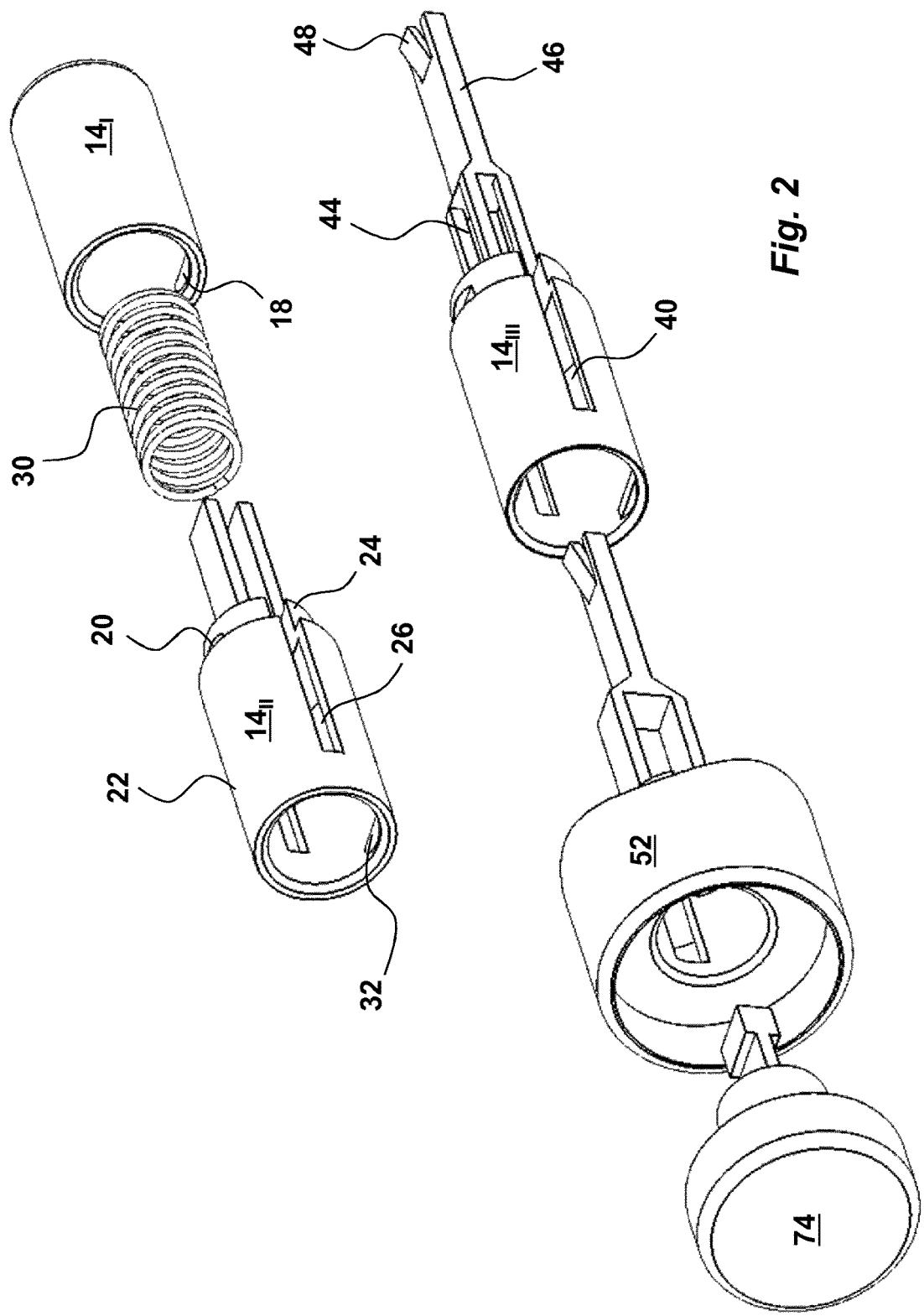
Figure 3:
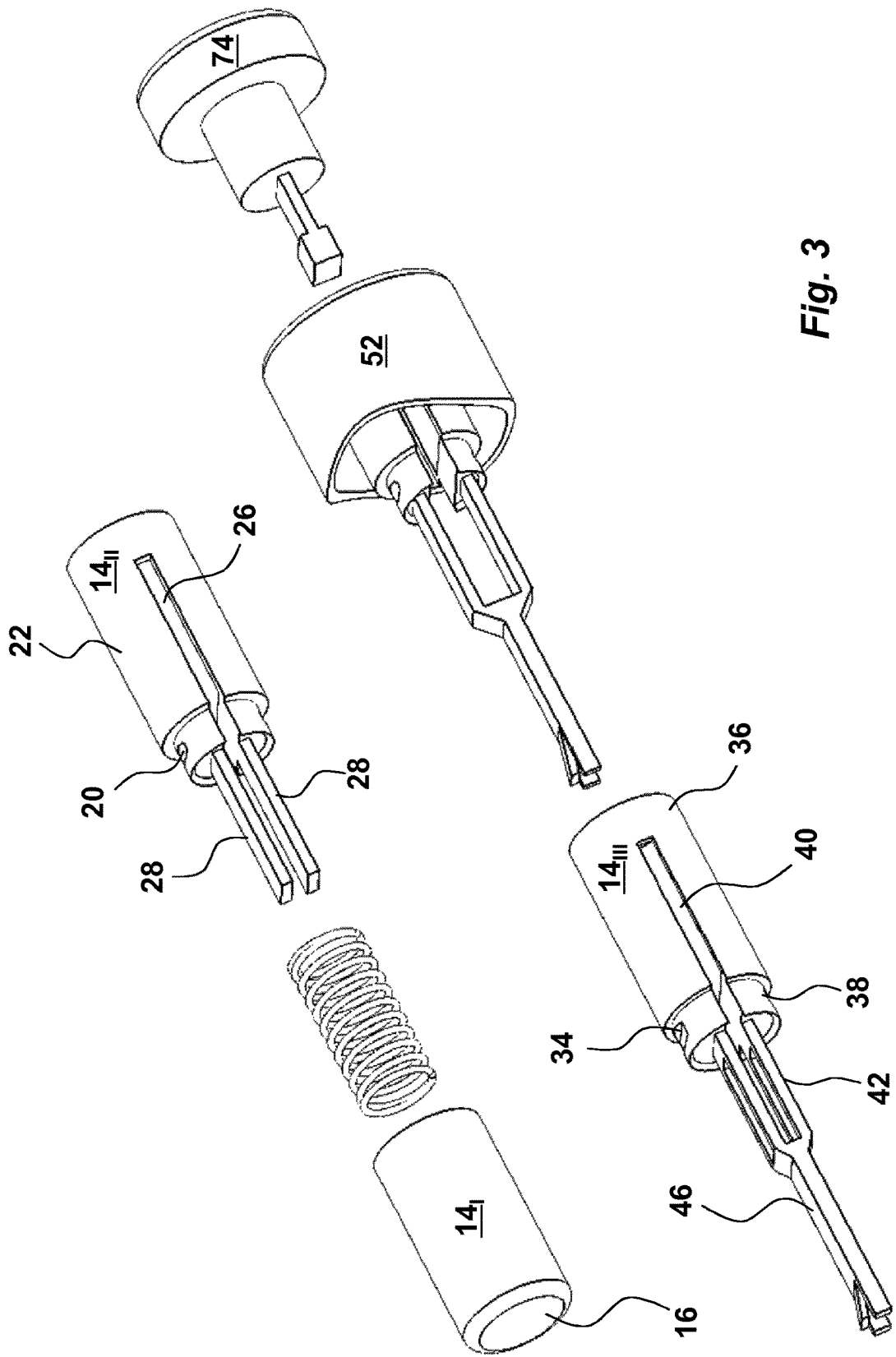

The protrusions 18 are intended to fit into corresponding interlocking elements, in the embodiment shown recesses 20 having mating structures positioned on a second segment $14_{II}$. The second segment $14_{II}$ comprises a generally tubular main body 22. At the proximal end of the body 22, a circumferential protrusion, or ledge, 24 is arranged. The ledge 24 has a diameter generally corresponding to the inner diameter of the passage 17 of the first segment $14_I$ so that the first segment $14_I$ fits with the second segment $14_{II}$. Further the circumferential ledge 24 is provided with the recesses 20, whereby a releasable locking function is provided between the segments. Further, the main body 22 and the ledge 24 are arranged with a longitudinal slit 26, dividing the ledge 24 into two generally longitudinal opposing parts and ending at a distance from a distal end surface of the main body 22. Further, two proximally directed arms 28 are arranged on the proximally directed end surface of the ledge 24 on each side of the slit 26. The arms 28 are designed with flat rectangular shapes as seen in FIGS. 2 and 4. A drive force element, e.g. a drive spring 30, is arranged between the proximally directed end surface of the ledge and a distally directed surface of the end wall 16 of the first segment $14_I$, as seen in FIG. 4b.

A third segment $14_{III}$ is connected to the second segment $14_{II}$, FIG. 5. The second segment is therefore arranged with two protrusions 32, FIGS. 2 and 5a, on an inner surface of a passage 33 of the main body 22, where the protrusions 32 are arranged on diametrically opposite sides. These protrusions 32 are arranged to cooperate with recesses 34 arranged on the third segment $14_{III}$. In this respect, the third segment has a similar design as the second segment regarding a main body 36 provided with a proximally directed protrusion, or ledge, 38, on which ledge 38 the recesses 34 are arranged. Further, a longitudinal slit 40 is arranged in the same manner, ending a distance before the distal end of the main body 36 and dividing the ledge 38 in two parts. As with the previous segment two rectangularly shaped arms 42 extend from the proximal end wall of the ledge 38.

However, the rectangular arms 42 extending in the proximal direction are arranged with rectangular cut-outs 44, FIG. 2. Further, the proximal ends of the rectangular arms 42 are interconnected with a bridge 45, and one rectangular arm 46 extends in the proximal direction from the bridge 45. At the proximal end of the rectangular arm 46, a support element, in the embodiment shown a tongue 48 is arranged with an inclination in relation to the longitudinal direction, extending in the proximal direction. When the third segment $14_{III}$ is assembled with the second segment $14_{II}$, the single rectangular arm 46 is positioned in the gap between the rectangular arms 28 of the second segment $14_{II}$, wherein the tongue 48 will be biased to a position parallel with the arms 28 as seen in FIG. 5b. The position of the single arm 46 of the third segment $14_{III}$ in the gap of the second segment $14_{II}$ will prevent any flexing of the ledge 24 of the second segment $14_{II}$ in the inwards radial direction, thereby locking the protrusions 18 of the first segment $14_I$ in the recesses 20 of the second segment $14_{II}$ and thereby locking the first segment $14_I$ to the second segment $14_{II}$ against the force of the drive spring 30. Further, a second drive spring 50 is arranged between the proximally directed end surface of the ledge of the third segment and a distally directed surface of the main body.

Depending on the length of the plunger rod 12 to be used, a number of third segments $14_{III}$ are used and interconnected as a described above. For instance, the plunger rod 12 shown in FIG. 1 has three segments of the third type. The single arm of a subsequent segment will be placed in the gap between the two rectangular arms of a previous segment, thereby preventing any flexing of the ledge in the inwards radial direction. However, due to the rectangular cut-outs 44 in the arms 42 from the ledge 38, the tongue 48 of the third segment is inclined into the cut-out 44.

The plunger rod is terminated at its distal end by an activation segment 52, FIG. 6. In the embodiment shown, it comprises a main body 54, which could be a part of a housing of a medicament delivery device. The main body 54 is arranged with a generally tubular central, section 56. In the proximal end of the tubular section a protrusion, or ledge, 58 is arranged, having generally the same design as the ledges of the previous segments. Thus, the ledge 58 is arranged with recesses 60 intended to accommodate protrusions 62 on an inner surface of a distal passage 63 of an adjacent third segment $14_{III}$. A slit 64 is further arranged in the central section 56 and divides the ledge 58 in two parts in the same manner as the previous segments.

The ledge 58 is further arranged with the same type of arm design as described above, thus two rectangular arms 66 interconnected with a bridge 67 at their proximal ends, from which bridge 67 a single, proximally directed, rectangular, arm 68 extends. The single rectangular arm 68 is arranged with an inclined flexible tongue 70. As seen in FIG. 6b, the gap g between the two rectangular arms 66 is larger than the width w of the slit. A compression spring 71 is further arranged in the same manner as described above, thus being tensioned between a proximally directed end surface of the ledge 58 and a distally directed surface of the body 36 of the previous third segment $14_{III}$.

Figure 7A:
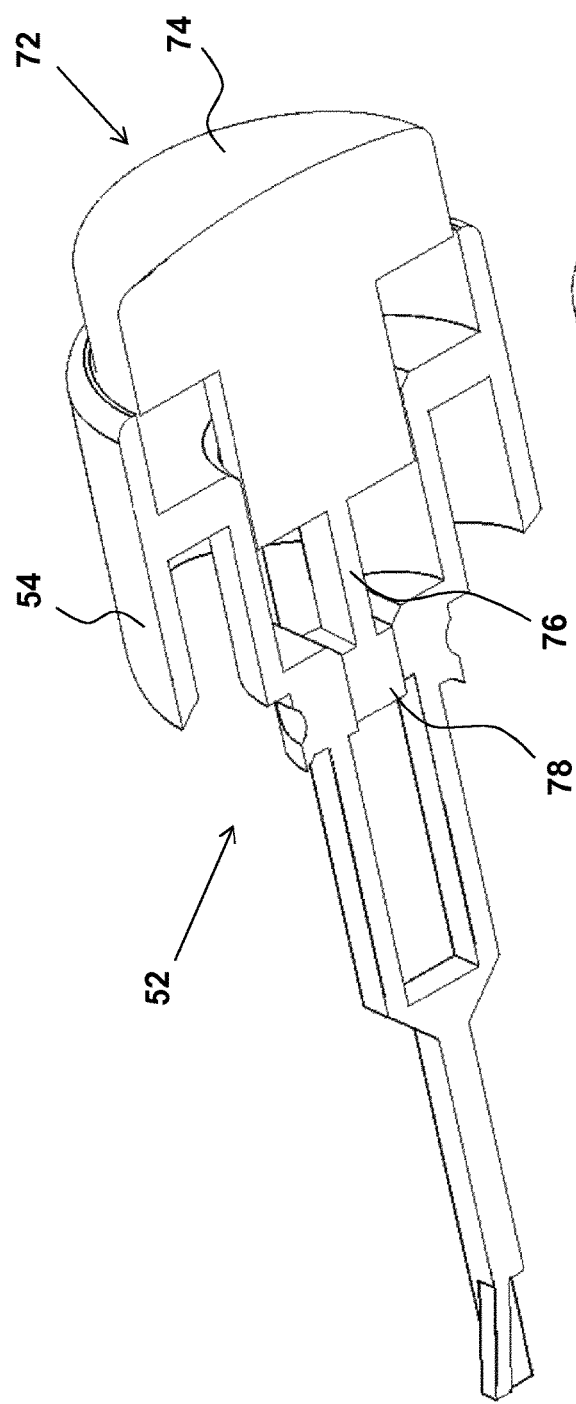

An actuator 72 is arranged to the activation segment, FIG. 7. It comprises in the embodiment shown a push button 74 extending in the distal direction from the main body 54 of the activation segment 52 such that it may be operated by a user. The push button 74 is arranged with a proximally directed arm 76, which arm 76 is arranged with radially extending ledges 78 that fit in the slit 64 of the activation segment 52 as seen in FIG. 7a, such as to prevent flexing of the ledge 58 of the activation segment 52 in the radial direction in the same manner as described above, thus locking the activation segment to the previous plunger rod segment.

Figure 7B:
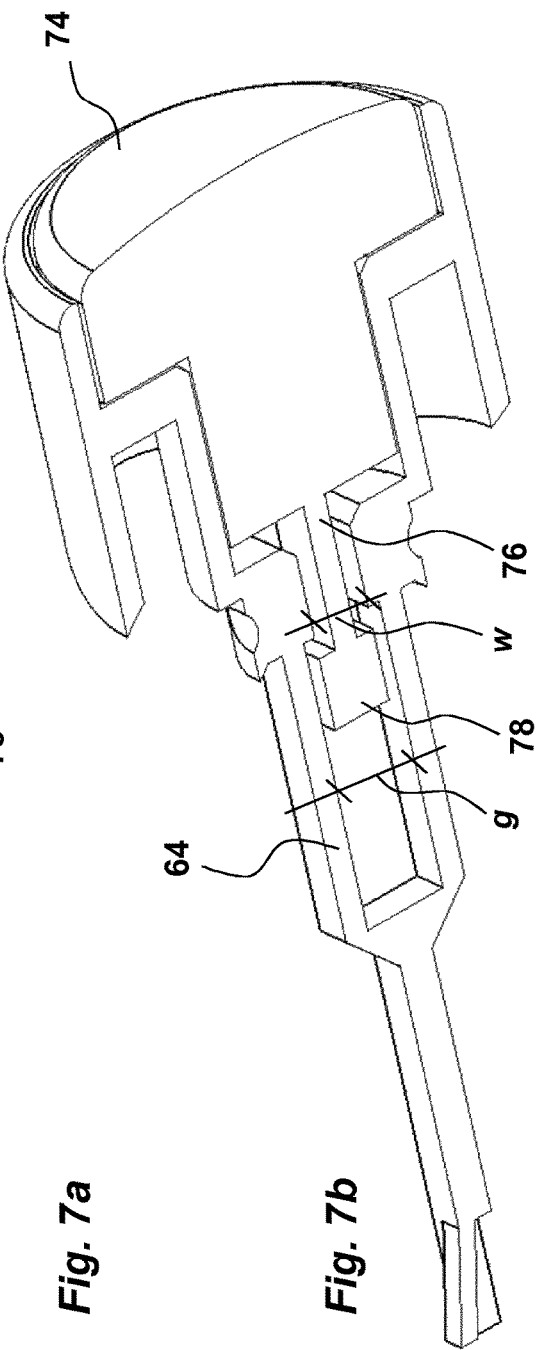

The plunger rod 12 according to the invention is intended to function as follows. When the drive mechanism is loaded and ready to be used, all segments are locked to each other by the protrusions of a proximally positioned segment fitting into recesses of an adjacent, distally positioned segment. The ledges of the segments are further prevented from flexing radially inwards due to the rectangular arms of an adjacent, distally positioned segment, placed in the gaps of an adjacent proximally positioned segment. The most distal segment is locked by the activation segment, as seen in FIG. 8a. When a user presses on the push button 74 of the actuator 72 in the proximal direction, FIGS. 7b and 8b, the ledges 78 of the arm 76 of the actuator 72 are moved out of contact with the slit walls and into the gap g between the rectangular arms 66 as seen in FIG. 7b. Because the gap g is larger than the width w of the slit, the ledge 58 may flex inwards due to the slit 64, and due to the force of the compression spring 71, the protrusions 62 of the adjacent proximally positioned third segment $14_{III}$ will move out of contact with the recesses 60 of the activation segment 52.

Figure 10:
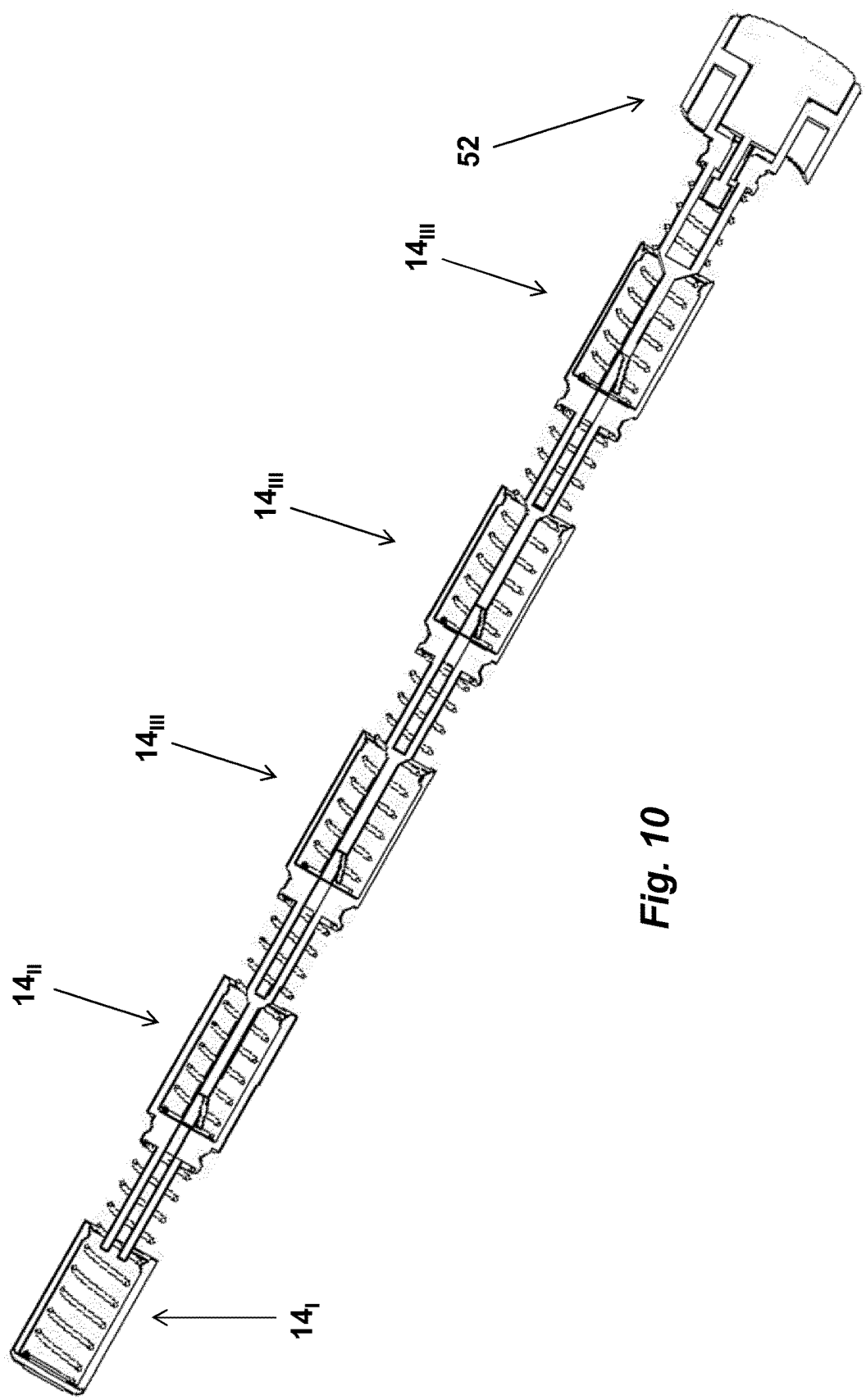

The proximally positioned segment and all the segments down to the first segment are now moving in the proximal direction, FIG. 9, for example acting on a stopper of a medicament container for expelling a dose of medicament. During the movement in the proximal direction the single rectangular arm 68 of the activation segment 52 is moved relative to the rectangular arms 42 and the ledge 38 of the previous segment until it is moved out of the slit 40 of the ledge 38 of the adjacent proximally positioned segment, whereby the tongue 70 of the activation segment 52 can flex out in the inclined position, FIG. 9b. Now the ledge 38 of the proximally adjacent segment is free to flex inwards and due to the force of the drive spring 50, the protrusions 62 of the subsequent proximally positioned segment are moved out of contact with the recesses 34 of the inwards-flexing ledge 38, thus forcing all the segments proximal to the inwards-flexing ledge 38 in the proximal direction. The inclined tongue 70 now acts as a stop against a distally directed surface of the previous segment, as seen in FIG. 9b, preventing movement in the distal direction of the more distal segment due to the force from the drive spring 50. The sequence then continues in the same manner by releasing segments successively and sequentially as the segments are moved in the proximal direction until the first segment $14_I$ is released and is moved to its end position as seen in FIG. 10.

Because of the plurality of segments and their drive springs, a more even force distribution is obtained throughout the movement of the plunger rod in comparison to a conventional single spring. It is also possible to have different force characteristics on some of the drive springs in order to obtain different functions depending on different force requirements during the movement of the plunger rod.

Figure 13A:
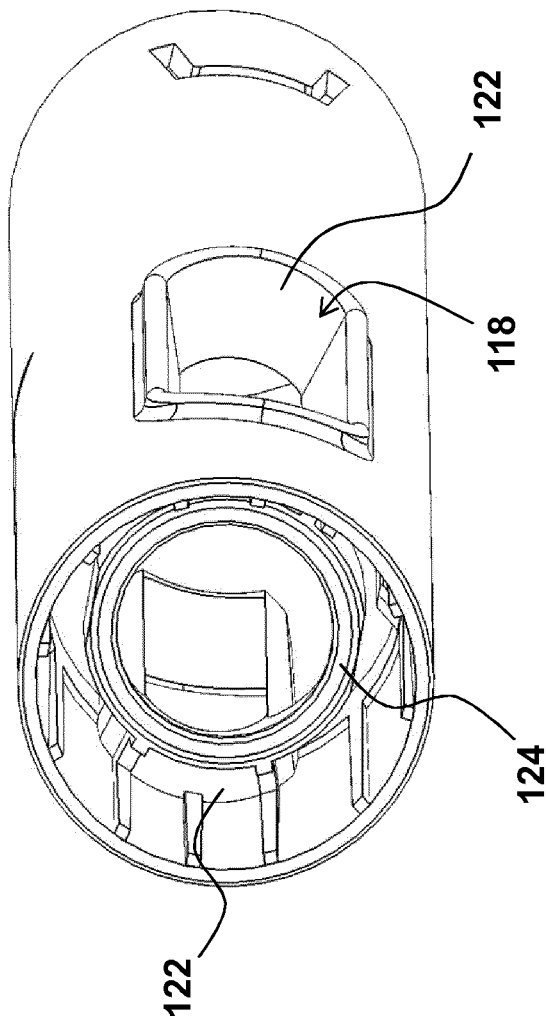
Figure 13B:
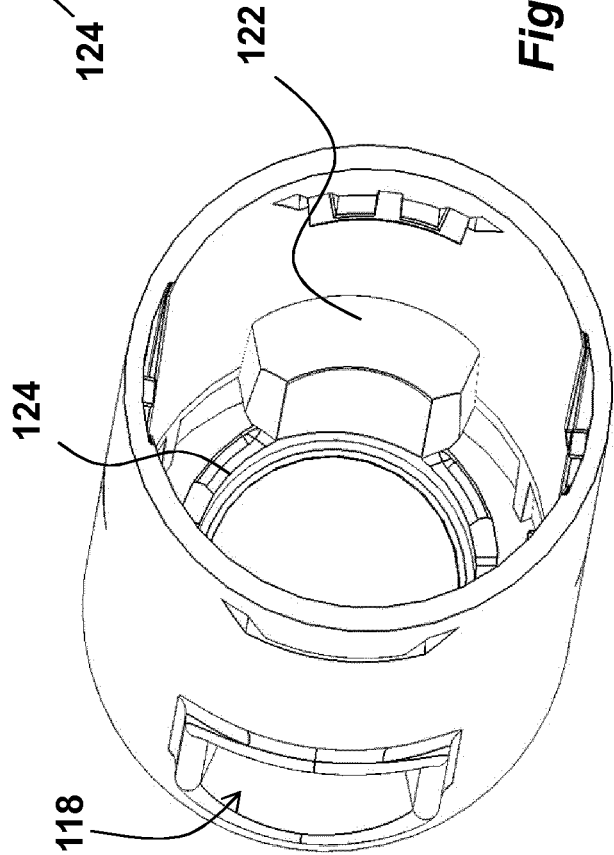

An exemplary medicament delivery device, comprising an embodiment of the drive mechanism according to the invention, will now be described. The medicament delivery device shown in the drawings 11-29 comprises a generally tubular elongated housing 110 having a distal end 112 and a proximal end 114. The housing 110 is further arranged with windows or openings 118, FIGS. 11 and 13, through which a medicament container 120 can be viewed. Each opening 118 is arranged with an inwardly directed circumferential ledge 122, FIG. 13. A ring-shaped support element 124 is further attached to the ledges 122 of the openings 118. The device further comprises a medicament container holder 126 having a generally tubular shape, FIG. 11. The medicament container holder is arranged to be supported in the generally radial direction by the ledges 122 of the openings and in the generally longitudinal direction by the ring-shaped support element 124.

Figure 12:
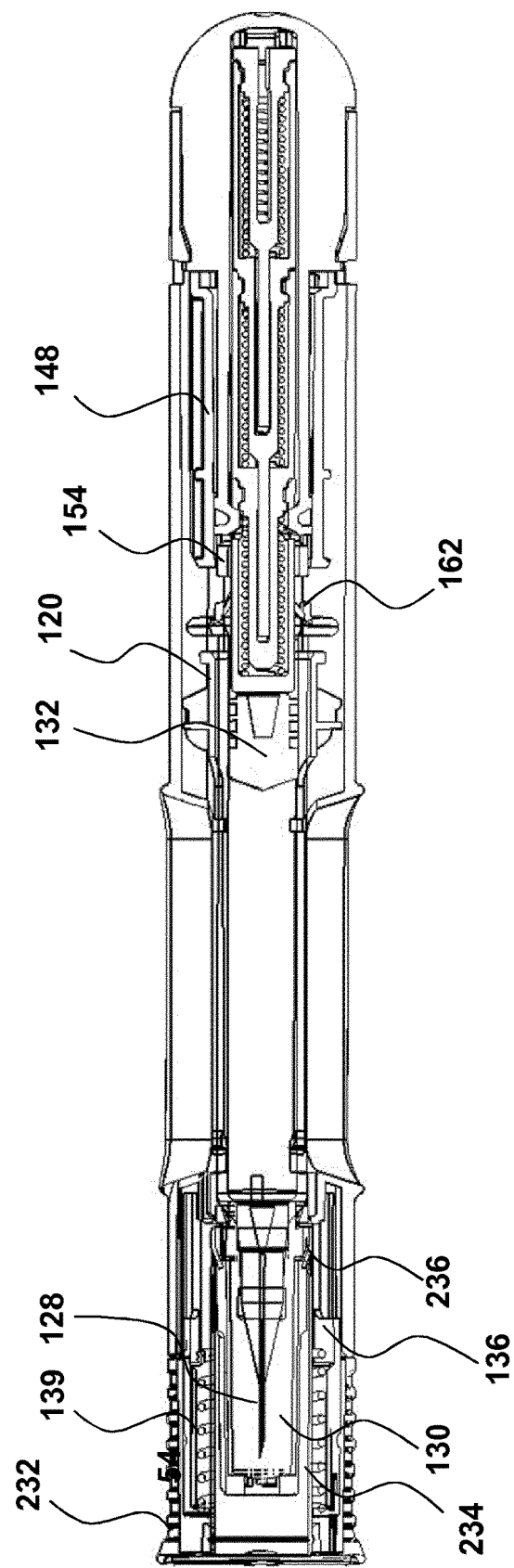
FIG. 12 shows a longitudinal cross-sectional view of the device of FIG. 11, FIGS. 13-22 show detailed views of components comprised in the device of FIG. 11, and FIGS. 23-28 show different functional views of the device of FIG. 11.

The medicament container holder is arranged to accommodate the medicament container 120, where the medicament container 120 has a proximal end to which a medicament delivery member 128, FIG. 12, is attached, either made integral or connectable to the medicament container. The medicament delivery member is preferably protected before use by a medicament delivery member shield 130, in the embodiment shown, a so called rigid needle shield or RNS. It is however to be understood that other types of medicament delivery member shields may be used in order to obtain the desired protection of the medicament delivery member. The medicament container 120 is further arranged with a movable stopper 132, FIG. 12.

Figure 11:
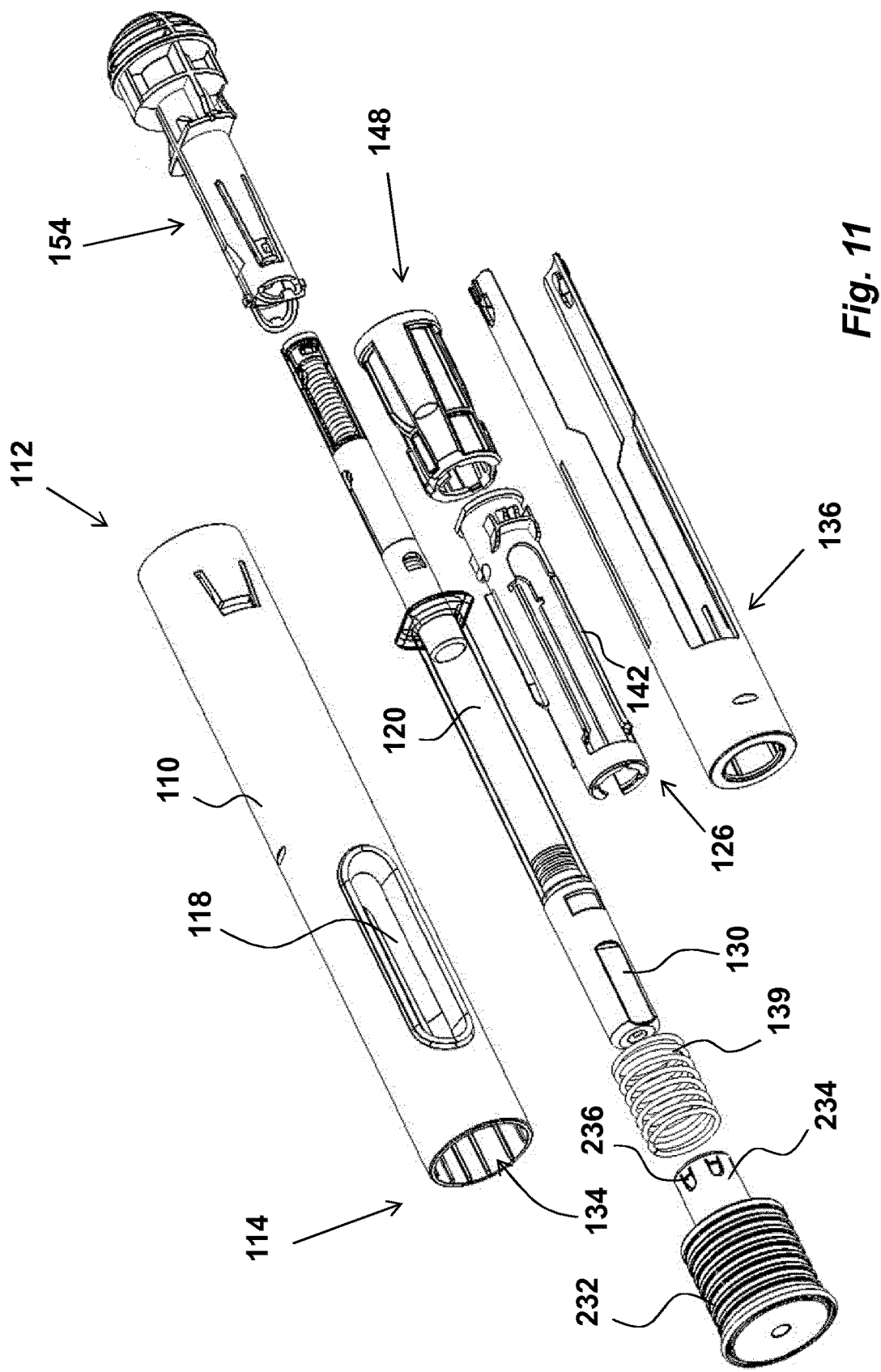
FIG. 11 shows an exploded view of a medicament delivery device provided with a drive mechanism according to the present invention.
Figure 14:
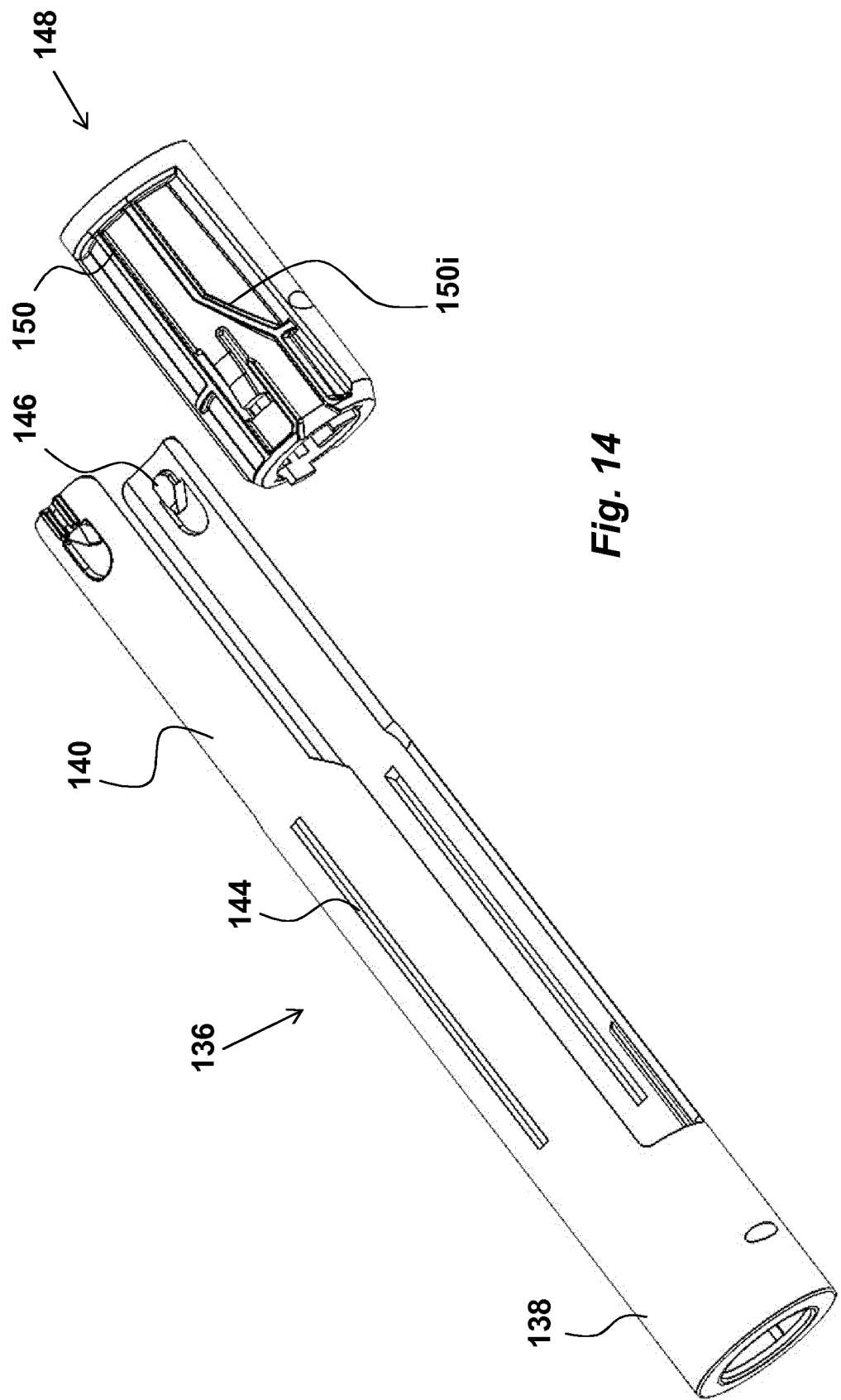

The proximal end of the housing is arranged with a central passage 134, FIG. 11, through which a generally tubular medicament delivery member guard 136 extends, FIGS. 11 and 14. The medicament delivery member guard 136 is arranged slidable in the housing 10. The medicament delivery member guard comprises a proximal tubular part 138 and two distally directed arms 140 extending from the tubular part 138. A medicament delivery member guard spring 139 is arranged between a distally directed circumferential wall part of the medicament delivery member guard 136 and a proximally directed circumferential surface of the housing as seen in FIG. 12. The arms 140 are arranged slidable along the medicament container holder and are guided by elongated ledges 142, FIG. 11, on the outer surface of the medicament container holder 126 fitting into elongated grooves 144 in the arms 140. At the distal end of the arms, inwardly directed protrusions 146 are arranged. The protrusions are arranged to operably interact with a rotator 148, FIGS. 14 and 15, in turn positioned distally of the medicament container 120.

The rotator 148 has a generally tubular shape and is arranged with guides 150 that are intended to cooperate with the protrusions 146 of the medicament delivery member shield 136 as will be described, wherein some sections $150_i$ of the guide ridges are inclined in relation to the longitudinal direction of the device. The rotator is further arranged with wedge-shaped protrusions 152 arranged on generally radially flexible tongues 153, positioned adjacent the guide ridges 150, which wedge-shaped protrusions 152 are intended to lock the medicament delivery member guard 136 after completed use of the device as will be described.

An actuator 154, FIG. 16, is further arranged operably to the rotator 148. It comprises a first proximal tubular section 156 having a diameter slightly smaller than the inner diameter of the rotator 148. Distally to the first proximal tubular section 156 It further comprises a second section 158 arranged to fit into and to be attached to a distal part of the housing. The second section 158 terminates in an end cap 160 that in the embodiment shown is dome-shaped. The first section 156 is further arranged with holding elements 162, shown as arch-shaped elements extending in the proximal direction from a proximal end surface of the first section 156. The holding elements 162 are arranged press against a distal circumferential end surface of the medicament container 120 when placed in the medicament container holder 126, FIG. 12.

Figure 15B:
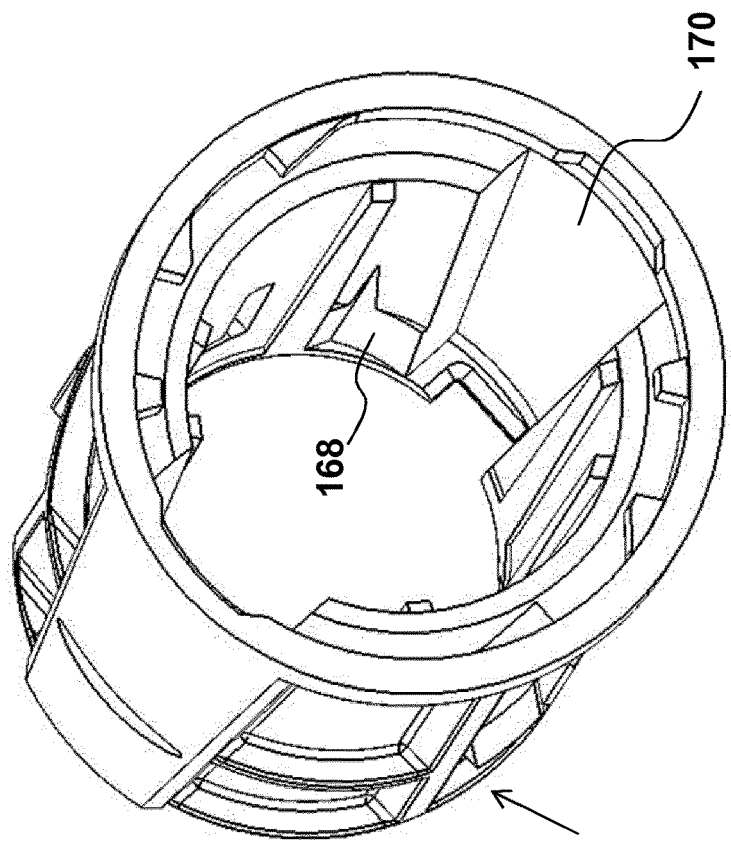
Figure 15A:
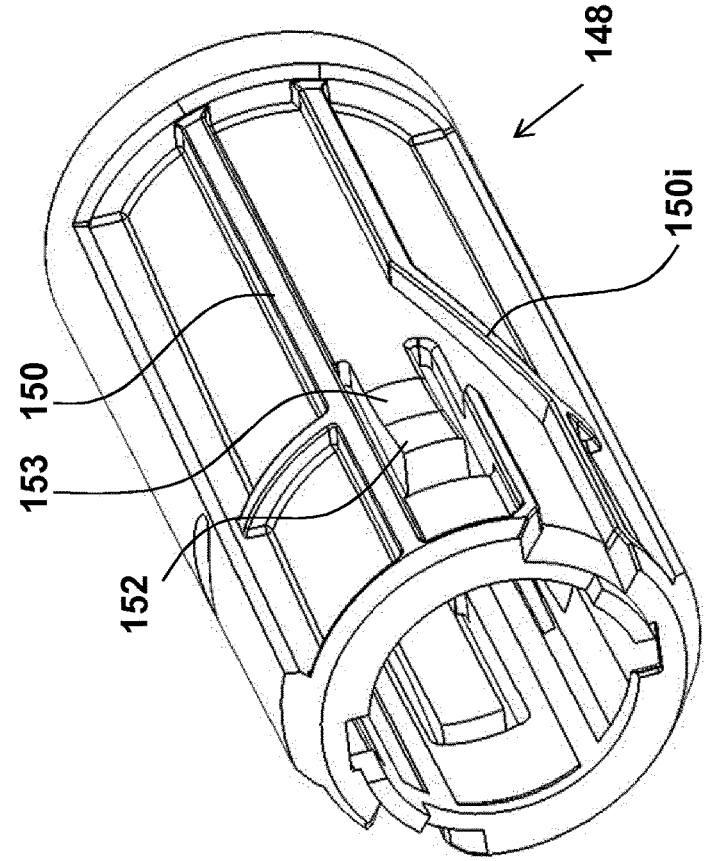

Further, a circumferential wall of the first section 156 is arranged with proximally extending arms 164 that are arranged flexible in a generally radial direction. The free ends of the arms 164 have outwardly extending protrusions 166 that are to interact with inner surfaces of the rotator 148 as will be described. In that respect, the rotator 148 is arranged with support surfaces 168 as well as longitudinally extending recesses 170 adjacent the support surfaces 168 as seen in FIG. 15, wherein the support surfaces 108 as well as the recesses 170 will interact with the outwardly extending protrusions 166, as will be described. Further the free ends of the arms 164 are arranged with inwardly extending protrusions 172, which protrusions 172 are intended to interact with recesses 174 on a plunger rod 176 of a drive mechanism 177 according to the invention, FIG. 16b.

The plunger rod 176 of the drive mechanism 177 is arranged as a number of discrete segments 178, FIG. 16b. A first segment $178_I$, FIG. 17, the most proximal, is arranged as a generally tubular body 179 having a proximal end surface 180 intended to be in contact with the stopper 132 of the medicament container 120. The tubular body 179 is arranged with interlocking elements as described above. Therefore, an inner surface of a distal passage 181 of the first segment $178_I$ is arranged with two protrusions 182, positioned opposite each other. These protrusions 182 are intended to interact with recesses 184 of a circumferential protrusion, or ledge, 186, of a second segment $178_{II}$. The ledge 186 of the second segment $178_{II}$ is attached to, or made integral with, a generally tubular main body 187. A major part of the tubular body 187 and the ledge 186 are split in two halves by a longitudinally extending slit 188, providing flexibility of the halves in the generally radial direction. The ledge 186 is further arranged with two proximally extending arms 190, one on each side of the slit 188. The arms 190 are joined at their proximal ends by a bridge 192. The ledge 186 is also arranged with generally arc-shaped protrusions 193 adjacent the arms 190 as seen in FIGS. 18 and 19, the function of which will be described below.

A drive force element, a spring 194 is further arranged between a distally facing surface of the end surface 180 of the first segment $178_I$ and the arc-shaped protrusions 193 and. FIG. 19 shows schematically how the spring, indicated by the dotted line, is positioned in relation to the arc-shaped protrusions 193 and FIG. 20 shows the spring 194 in contact with the arc-shaped protrusions 193. The main body of the second segment $178_{II}$ is further arranged with two protrusions 196 on an inner wall of a distal passage 197, FIG. 17, arranged opposite each other. These protrusions 196 are intended to interact with recesses 198 on a circumferential protrusion, or ledge, 200 of a third segment $178_{III}$, FIG. 21.

The third segment $178_{III}$, FIG. 21, generally has the same shape and features as the second segment $178_{II}$. That is, a slit 202 is arranged in the body and the ledge. Two proximally extending arms 204 are integrated in the ledge 200 on each side of the slit 202. The arms 204 are connected to each other at the proximal end by a bridge 206. One additional feature that the third segment $178_{III}$ is arranged with is a proximally extending rectangularly shaped arm 208 attached to or made integral with the bridge 206.

Arc-shaped protrusions 209 are arranged adjacent the arms 204 in the same manner as with the second segment $178_{II}$ as seen in FIG. 22. A drive spring 210 is arranged between the second and the third segment in the same manner as described earlier, i.e. between a distally directed wall of the second segment $178_{II}$ and the arc-shaped protrusions 209 of the third segment $178_{III}$.

Protrusions 212 on an inner wall of a distal passage 213 of the third segment $178_{III}$ are designed to cooperate with recesses 214 on an end segment 216 of the plunger rod 176, FIG. 21. The end segment 216 comprises an end plate 218 arranged with a proximally extending protrusion, or ledge, 220, which ledge 220 has a diameter generally corresponding to the inner diameter of the third segment $178_{III}$ and wherein the recesses 214 are placed on the ledge 220.

A slit 222 divides the end plate 218 and the ledge 220 in the same manner as described earlier. Two arms 224 extend in the proximal direction from the ledge. 220. The two arms 224 are joined at their proximal ends by a bridge 226. A generally rectangular arm 228 extends in the proximal direction from the bridge 226. A drive spring 230 is arranged between the ledge 220 of the end segment 216 and the third segment $178_{III}$. The distally directed surface of the end plate is in contact with proximally directed support ledges 231 of the end cap 160, FIG. 23.

Finally, the medicament delivery device is arranged with a protective cap 232, FIGS. 11 and 12, connectable to the proximal end thereof. The protective cap 232 extends with a tubular part 234 into the medicament delivery member guard 136 and surrounds the medicament delivery member shield 130. The inner surface of the tubular part 234 is arranged with grip elements 236 capable of gripping the medicament delivery member shield 130.

The device is intended to function as follows. When the device is delivered to the user, the segments 178 of the plunger rod 176 are attached to each other by the interlocking elements, i.e. the protrusions 182, 196, 212 of a proximal segment fitting into the recesses 184, 198, 214 of a distal segment, FIG. 24. Since the release elements, i.e. the generally rectangular proximally directed arm 208, 228 of a distal segment and the end segment 216 is placed in the gap of a proximal segment, the ledges 186 and 200 cannot flex in the generally radial direction, FIG. 24. The drive force elements, i.e. the drive springs 194, 210, 230 of the plunger rod are tensioned and the plunger rod is held in this tensioned stated by the inwardly directed protrusions 178 fitting into the recesses 174 of the first plunger rod segment $178_I$, FIG. 24. A medicament container 120 has been loaded into the medicament container 126 and placed in the housing of the device. The proximal end of the medicament container has been provided with a protective cap 232 at its proximal end. In order to activate the device, the protective cap 232 is removed by pulling it in the proximal direction. This causes the grip elements 236 to grip into and remove the medicament delivery member shield 130 from the medicament delivery member 128. The medicament delivery member guard 136 is held in its most proximal position by the medicament delivery member guard spring 139.

The user now presses the proximal end of the device with the medicament delivery member guard 136 against a dose delivery site and when an injection needle is used as a medicament delivery member 128, the users skin is penetrated by the needle. The penetration is caused by the housing, and consequently the medicament container and delivery member, moving in the proximal direction in relation to the medicament delivery member guard 136. The relative movement of medicament delivery member guard in turn causes the protrusions 146 of the medicament delivery member guard 136 to move along the guide ridges 150 of the rotator such that the protrusions will come in contact with the inclined sections $150_i$, which will cause the rotator 148 to turn around the longitudinal axis of the device.

The turning of the rotator 148 will cause the outwardly extending protrusions 166 of the actuator 154 to move out of contact with the support surfaces 168 of the rotator 148 and into its recesses 170. The arms 164 of the actuator 154 are now free to flex outwardly, whereby the inwardly directed protrusions 172 of the arms 164 are moved out of contact with the recesses 174 of the first segment $178_I$ of the plunger rod 176. The force of the most distal drive spring 230 acting on the adjacent proximally positioned segment will cause its protrusions 212 to move out of contact with the recesses 214 of the end segment 216 since there is nothing preventing the flexing of the ledge 220 in the radial direction due to the slit 222. The end segment 216 is further prevented from moving in the distal direction by the force of the drive spring 230 due to the support ledges 231 of the end cap.

The plunger rod segments $178_I$, $178_{II}$ and $178_{III}$ will then be urged in the proximal direction by the most distal drive spring 230, FIG. 21. During the movement of the plunger rod segments in the proximal direction, the rectangular arm 228 of the end segment 216 will move out of contact with the slit 202 of the proximally positioned segment $178_{III}$, FIG. 24. This will allow the ledge 200 of the third segment $178_{III}$ to flex radially inwards and in turn the second segment $178_{II}$ will be released from the third segment $178_{III}$ and urged in the proximal direction by the drive spring 210 arranged between the third and the second segment, FIG. 24. The flexing of the ledge 200 in the radial direction will cause the spring 210 to "roll" or slide off the arc-shaped protrusions 209, FIGS. 25 and 26, whereby the arc-shaped protrusions 209 will enter the spring, and wherein the spring will abut the ledge 200. This in turn causes the gap of the slit 202 to be reduced such that the proximal end surface of the arm 228 of the end segment 216 will act as a support surface for the third segment $178_{III}$, preventing it to be moved in the distal direction by the drive spring 210.

The third segment $178_{III}$ has now stopped its motion in the proximal direction and this will cause its arm 208 to move out of contact with the gap 188 of the second segment $178_{II}$ when the second segment has reached a certain position in the proximal direction, FIG. 27. As previously described, this allows the ledge of the second segment $178_{II}$ to flex radially inwards, whereby the protrusions of the first segment $178_I$ will move out of contact with the recesses of the second segment. Also as previously described, the spring will slide off the arc-shaped protrusions 193 of the second segment, reducing the gap of the slit 188. The proximal end surface of the arm 208 of the third segment $178_{III}$ will now act as stop surface of the second segment $178_{II}$, preventing it to be moved in the distal direction by the drive spring 194. The drive spring 194 between the second segment $178_{II}$ and the first segment $178_{I}$ now urges the first segment $178_{I}$ in the proximal direction until the stopper 132 of the medicament container reaches its most proximal position as seen in FIG. 28.

The dose delivery sequence is now completed and the device may be removed from the dose delivery site. The medicament delivery member guard is now urged in the proximal direction by the medicament delivery member guard spring in relation to the housing 110. This in turn causes the protrusions 146 of the arms 140 to move along the guide ridges 150 of the rotator 148, whereby the protrusions 146 will pass the wedge-shaped protrusions 152 due to the flexing action of the tongues 153. The passing of the protrusions 152 will cause the medicament delivery member guard 136 to be locked in its extended position, thereby preventing any unintentional contact and possible injury with the medicament delivery member. The device may now be discarded in a safe manner.

It is to be understood that the embodiment described above and shown in the drawings is to be regarded only as a non-limiting example of the invention and that it may be modified in many ways within the scope of the patent claims.

The invention claimed is:

1. A drive mechanism for a medicament delivery device, wherein the drive mechanism comprises an elongated plunger rod, wherein the plunger rod comprises a number of discrete segments, interlocking elements arranged between adjacent segments operably arranged to releasably lock adjacent segments, drive force elements operably arranged to act between adjacent segments, and release elements operably arranged to act on the interlocking elements such that the segments are released in sequence,
   wherein the interlocking elements comprise form-engaging elements, and
   wherein the interlocking elements comprise interlocking protrusions and recesses arranged on adjacent segments, the protrusions and recesses arranged generally radially in relation to each other.

2. The drive mechanism according to claim 1, wherein the interlocking elements are arranged such that the radially innermost of the interlocking elements is movable inwards in the generally radial direction.

3. The drive mechanism according to claim 2, wherein the release elements are operably connected to the innermost interlocking elements such as to prevent movement inwards until activation of the drive mechanism.

4. The drive mechanism according to claim 3, wherein the release element is a part of an adjacent, distally positioned, segment.

5. The drive mechanism according to claim 4, wherein a segment is arranged with a passage in its distal end, that an adjacent, distally positioned, segment is arranged with a protrusion fitting into the passage, the protrusion fitting comprising the release elements.

6. The drive mechanism according to claim 5, wherein the protrusion fitting is arranged flexible in a generally radial direction and wherein the release elements comprise an elongated element in contact with the protrusion fitting for preventing flexing in the generally radial direction.

7. The drive mechanism according to claim 6, wherein the flexible arrangement comprises a generally longitudinally extending slit, the slit dividing the protrusion fitting in at least two parts, and wherein the elongated element extends into the slit.

8. The drive mechanism according to claim 1, further comprising support elements arranged to support a segment when a proximally positioned segment has been distally displaced.

9. The drive mechanism according to claim 8, wherein the support elements are arranged to prevent movement in the distal direction.

10. The drive mechanism according to claim 8, wherein the support elements are comprised in the elongated element, the support elements comprising a proximally directed surface.

11. The drive mechanism according to claim 10, wherein the proximally directed surface is arranged on a flexing arm that flexes in a generally transversal direction when the elongated element is moved out of contact with the slit.

12. The drive mechanism according to claim 10, wherein the drive force elements are operably arranged such that the gap of the slit is reduced when the elongated element is moved out of the slit.

13. The drive mechanism according to claim 1, wherein characteristics of the drive force elements are selected independently for meeting injection force requirements.

14. A medicament delivery device comprising a drive mechanism according to claim 1.

* * * * *